(12) United States Patent
Ludwig et al.

(10) Patent No.: US 7,717,939 B2
(45) Date of Patent: May 18, 2010

(54) ROD ATTACHMENT FOR HEAD TO HEAD CROSS CONNECTOR

(75) Inventors: Steven Ludwig, Baltimore, MD (US); Mark T. Hall, Bridgewater, MA (US); Thomas V. Doherty, Latham, NY (US)

(73) Assignee: Depuy Spine, Inc., Raynham, MA (US)

( * ) Notice: Subject to any disclaimer, the term of this patent is extended or adjusted under 35 U.S.C. 154(b) by 1072 days.

(21) Appl. No.: 11/162,934

(22) Filed: Sep. 28, 2005

(65) Prior Publication Data

US 2006/0064091 A1 Mar. 23, 2006

Related U.S. Application Data

(63) Continuation-in-part of application No. 10/813,904, filed on Mar. 31, 2004.

(51) Int. Cl.
*A61B 17/70* (2006.01)
(52) U.S. Cl. .................. 606/250; 606/246; 606/265; 606/266; 606/267
(58) Field of Classification Search .............. 606/250, 606/264–278; 623/17.11–17.16
See application file for complete search history.

(56) References Cited

U.S. PATENT DOCUMENTS

| | | | |
|---|---|---|---|
| 180,881 A | 8/1876 | Howson |
| 457,964 A | 8/1891 | Bolte |
| 483,342 A | 9/1892 | Bolte |
| 596,729 A | 1/1898 | White |
| 900,717 A | 10/1908 | Feaster |
| 1,455,441 A | 5/1923 | La Hodny |
| 2,638,301 A | 5/1953 | Smith |
| 3,019,504 A | 2/1962 | Castagliuolo |
| 3,499,222 A | 3/1970 | Linkow et al. |
| 3,752,203 A | 8/1973 | Hill, Jr. |
| 4,011,602 A | 3/1977 | Rybicki et al. |
| 4,085,744 A | 4/1978 | Lewis et al. |
| 4,179,905 A | 12/1979 | Schultenkamper |
| 4,289,124 A | 9/1981 | Zickel |
| 4,404,967 A | 9/1983 | Bacal et al. |
| 4,411,259 A | 10/1983 | Drummond |
| 4,611,580 A | 9/1986 | Wu |

(Continued)

FOREIGN PATENT DOCUMENTS

DE 867422 2/1953

(Continued)

OTHER PUBLICATIONS

Depuy AcroMed, "Modular Cross Connector (MCC)" brochure, 2000.

(Continued)

*Primary Examiner*—Thomas C Barrett
*Assistant Examiner*—Andrew Yang

(57) ABSTRACT

Exemplary spinal fixation devices, systems, and method are provided for stabilizing vertebrae in a patient's spine. In one exemplary embodiment, methods and devices are provided for coupling one or more bone anchors, such as hooks, screws, etc., and/or one or more spinal fixation elements, such as spinal rods, cables, plates, etc. In certain exemplary embodiments, a cross connector is provided for connecting and stabilizing two bone anchors, a bone anchor and a spinal fixation element, or a bone anchor and bone.

21 Claims, 26 Drawing Sheets

U.S. PATENT DOCUMENTS

| | | |
|---|---|---|
| 4,611,581 A | 9/1986 | Steffee |
| 4,611,582 A | 9/1986 | Duff |
| 4,641,636 A | 2/1987 | Cotrel |
| 4,648,388 A | 3/1987 | Steffee |
| 4,653,481 A | 3/1987 | Howland et al. |
| 4,655,199 A | 4/1987 | Steffee |
| 4,658,809 A | 4/1987 | Ulrich et al. |
| 4,696,290 A | 9/1987 | Steffee |
| 4,719,905 A | 1/1988 | Steffee |
| 4,743,260 A | 5/1988 | Burton |
| 4,759,769 A | 7/1988 | Hedman et al. |
| 4,763,644 A | 8/1988 | Webb |
| 4,771,767 A | 9/1988 | Steffee |
| 4,773,402 A | 9/1988 | Asher et al. |
| 4,805,602 A | 2/1989 | Puno et al. |
| 4,815,453 A | 3/1989 | Cotrel |
| 4,887,595 A | 12/1989 | Heinig et al. |
| 4,913,134 A | 4/1990 | Luque |
| 4,950,269 A | 8/1990 | Gaines, Jr. |
| 4,957,495 A | 9/1990 | Kluger |
| 5,002,542 A | 3/1991 | Frigg |
| 5,005,562 A | 4/1991 | Cotrel |
| 5,010,879 A | 4/1991 | Moriya et al. |
| 5,024,213 A | 6/1991 | Asher et al. |
| 5,030,220 A | 7/1991 | Howland |
| 5,067,955 A | 11/1991 | Cotrel |
| 5,084,049 A | 1/1992 | Asher et al. |
| 5,092,866 A | 3/1992 | Breard |
| 5,092,893 A | 3/1992 | Smith |
| 5,102,412 A | 4/1992 | Rogozinski |
| 5,113,685 A | 5/1992 | Asher et al. |
| 5,116,334 A | 5/1992 | Cozad et al. |
| 5,120,171 A | 6/1992 | Lasner |
| 5,127,912 A | 7/1992 | Ray et al. |
| 5,129,899 A | 7/1992 | Small et al. |
| 5,129,900 A | 7/1992 | Asher et al. |
| 5,133,716 A | 7/1992 | Plaza |
| 5,147,359 A | 9/1992 | Cozad et al. |
| 5,147,360 A | 9/1992 | Dubousset |
| 5,154,718 A | 10/1992 | Cozad et al. |
| 5,176,678 A | 1/1993 | Tsou |
| 5,176,680 A | 1/1993 | Vignaud et al. |
| 5,190,543 A | 3/1993 | Schlapfer |
| 5,207,678 A | 5/1993 | Harms et al. |
| 5,234,431 A | 8/1993 | Keller |
| 5,242,443 A | 9/1993 | Kambin |
| 5,261,907 A | 11/1993 | Vignaud et al. |
| 5,261,913 A | 11/1993 | Marnay |
| 5,275,600 A | 1/1994 | Allard et al. |
| 5,282,801 A | 2/1994 | Sherman |
| 5,282,863 A | 2/1994 | Burton |
| 5,304,177 A | 4/1994 | Pennig |
| 5,306,275 A | 4/1994 | Bryan |
| 5,312,405 A | 5/1994 | Korotko et al. |
| 5,330,473 A | 7/1994 | Howland |
| 5,334,203 A | 8/1994 | Wagner |
| 5,360,431 A | 11/1994 | Puno et al. |
| 5,366,455 A | 11/1994 | Dove et al. |
| 5,368,594 A | 11/1994 | Martin et al. |
| 5,387,213 A | 2/1995 | Breard et al. |
| 5,395,370 A | 3/1995 | Muller et al. |
| 5,397,363 A | 3/1995 | Gelbard |
| 5,403,316 A | 4/1995 | Ashman |
| 5,415,661 A | 5/1995 | Holmes |
| 5,419,522 A | 5/1995 | Luecke et al. |
| 5,423,818 A | 6/1995 | Van Hoeck et al. |
| 5,437,671 A | 8/1995 | Lozier et al. |
| 5,439,463 A | 8/1995 | Lin |
| 5,454,812 A | 10/1995 | Lin |
| 5,470,333 A | 11/1995 | Ray |
| 5,474,086 A | 12/1995 | McCormick et al. |
| 5,476,462 A | 12/1995 | Allard et al. |
| 5,487,742 A | 1/1996 | Cotrel |
| 5,496,321 A | 3/1996 | Puno et al. |
| 5,498,263 A | 3/1996 | DiNello et al. |
| 5,514,132 A | 5/1996 | Csernatony et al. |
| 5,522,816 A * | 6/1996 | Dinello et al. ............... 606/252 |
| 5,527,314 A | 6/1996 | Brumfield et al. |
| 5,531,745 A | 7/1996 | Ray |
| 5,534,002 A | 7/1996 | Brumfield et al. |
| 5,540,688 A | 7/1996 | Navas |
| 5,549,607 A | 8/1996 | Olson et al. |
| 5,556,431 A | 9/1996 | Buttner-Janz |
| 5,562,662 A | 10/1996 | Brumfield et al. |
| 5,562,663 A | 10/1996 | Wisnewski et al. |
| 5,562,737 A | 10/1996 | Graf |
| 5,571,191 A | 11/1996 | Fitz |
| 5,582,612 A | 12/1996 | Lin |
| 5,584,831 A | 12/1996 | McKay |
| 5,586,983 A | 12/1996 | Sanders et al. |
| 5,591,165 A | 1/1997 | Jackson |
| 5,601,552 A | 2/1997 | Cotrel |
| 5,609,592 A | 3/1997 | Brumfield et al. |
| 5,616,142 A | 4/1997 | Yuan et al. |
| 5,620,444 A | 4/1997 | Assaker |
| 5,624,442 A | 4/1997 | Mellinger et al. |
| 5,630,816 A | 5/1997 | Kambin |
| 5,651,789 A | 7/1997 | Cotrel |
| 5,662,853 A | 9/1997 | Hattori et al. |
| 5,667,506 A | 9/1997 | Sutterlin |
| 5,667,507 A | 9/1997 | Corin et al. |
| 5,669,910 A | 9/1997 | Korhonen et al. |
| 5,672,175 A | 9/1997 | Martin |
| 5,676,703 A * | 10/1997 | Gelbard ..................... 606/305 |
| 5,683,393 A | 11/1997 | Ralph |
| 5,688,272 A | 11/1997 | Montague et al. |
| 5,700,292 A | 12/1997 | Margulies |
| 5,704,936 A | 1/1998 | Mazel |
| 5,707,372 A | 1/1998 | Errico et al. |
| 5,709,684 A | 1/1998 | Errico et al. |
| 5,709,685 A | 1/1998 | Dombrowski et al. |
| 5,716,355 A | 2/1998 | Jackson et al. |
| 5,743,907 A | 4/1998 | Asher et al. |
| 5,743,911 A | 4/1998 | Cotrel |
| 5,752,955 A | 5/1998 | Errico |
| 5,776,135 A | 7/1998 | Errico et al. |
| 5,876,403 A | 3/1999 | Shitoto et al. |
| 5,885,284 A | 3/1999 | Errico et al. |
| 5,899,903 A | 5/1999 | Cotrel |
| RE36,221 E | 6/1999 | Breard et al. |
| 5,928,232 A | 7/1999 | Howland et al. |
| 5,937,363 A | 8/1999 | Saidi et al. |
| 5,947,966 A | 9/1999 | Drewry et al. |
| 5,961,516 A | 10/1999 | Graf |
| 5,980,521 A | 11/1999 | Montague |
| 5,980,523 A | 11/1999 | Jackson |
| 5,989,250 A | 11/1999 | Wagner et al. |
| 5,989,251 A | 11/1999 | Nichols |
| 6,063,089 A | 5/2000 | Errico |
| RE36,758 E | 6/2000 | Fitz |
| 6,083,226 A | 7/2000 | Fiz |
| 6,110,173 A | 8/2000 | Thomas, Jr. |
| 6,113,600 A | 9/2000 | Drummond et al. |
| 6,126,660 A | 10/2000 | Dietz |
| 6,132,464 A | 10/2000 | Martin |
| 6,136,003 A | 10/2000 | Hoeck et al. |
| 6,139,548 A | 10/2000 | Errico |
| 6,171,311 B1 | 1/2001 | Richelsoph |
| 6,217,578 B1 | 4/2001 | Crozet et al. |
| 6,234,705 B1 | 5/2001 | Troxell |
| 6,238,396 B1 | 5/2001 | Lombardo |
| 6,264,658 B1 | 7/2001 | Lee et al. |
| 6,267,764 B1 | 7/2001 | Elberg |
| 6,273,888 B1 | 8/2001 | Justis |

| | | | | | | |
|---|---|---|---|---|---|---|
| 6,283,967 | B1 | 9/2001 | Troxell et al. | 2004/0049275 A1 | 3/2004 | Reiley |
| 6,287,309 | B1 | 9/2001 | Baccelli et al. | 2004/0049276 A1 | 3/2004 | Reiley |
| 6,302,882 | B1 | 10/2001 | Lin | 2004/0049277 A1 | 3/2004 | Reiley |
| 6,315,779 | B1 | 11/2001 | Morrison et al. | 2004/0049278 A1 | 3/2004 | Reiley |
| 6,328,741 | B1 | 12/2001 | Richelsoph | 2004/0049281 A1 | 3/2004 | Reiley |
| 6,355,038 | B1 | 3/2002 | Pisharodi | 2004/0073215 A1 | 4/2004 | Carli |
| 6,402,751 | B1 | 6/2002 | Hoeck | 2004/0087949 A1 | 5/2004 | Bono et al. |
| 6,413,257 | B1 | 7/2002 | Lin | 2004/0111154 A1 | 6/2004 | Reiley |
| 6,419,703 | B1 | 7/2002 | Fallin | 2004/0116927 A1 | 6/2004 | Graf |
| 6,432,108 | B1 | 8/2002 | Burgess | 2004/0116928 A1 | 6/2004 | Young et al. |
| 6,440,169 | B1 | 8/2002 | Elberg et al. | 2004/0133203 A1 | 7/2004 | Young et al. |
| 6,602,253 | B2 | 8/2002 | Richelsoph | 2004/0143264 A1 | 7/2004 | McAfee |
| 6,524,310 | B1 | 2/2003 | Lombardo | 2004/0186474 A1 | 9/2004 | Matthis et al. |
| 6,551,318 | B1 | 4/2003 | Stahurski | 2004/0186475 A1 | 9/2004 | Falahee |
| 6,554,831 | B1 | 4/2003 | Rivard et al. | 2004/0236329 A1 | 11/2004 | Panjabi |
| 6,554,832 | B1 | 4/2003 | Shluzas | 2005/0033431 A1 | 2/2005 | Gordon et al. |
| 6,565,605 | B2 | 5/2003 | Goble | 2005/0033432 A1 | 2/2005 | Gordon et al. |
| 6,579,319 | B2 | 6/2003 | Goble | 2005/0033439 A1 | 2/2005 | Gordon et al. |
| 6,610,091 | B1 | 8/2003 | Reiley | 2005/0090821 A1 | 4/2005 | Berrevoets et al. |
| 6,616,668 | B2 | 9/2003 | Altarac et al. | 2005/0101954 A1 | 5/2005 | Simonson |
| 6,616,669 | B2 | 9/2003 | Ogilvie et al. | 2005/0101956 A1 | 5/2005 | Simonson |
| 6,641,583 | B2 | 11/2003 | Shluzas et al. | 2005/0102028 A1 | 5/2005 | Arnin et al. |
| 6,645,207 | B2 | 11/2003 | Dixon | 2005/0113927 A1 | 5/2005 | Malek |
| 6,669,729 | B2 | 12/2003 | Chin | 2005/0119657 A1 | 6/2005 | Goldsmith |
| 6,673,073 | B1 | 1/2004 | Schafer | 2005/0228326 A1 | 10/2005 | Kalfas et al. |
| 6,689,133 | B2 | 2/2004 | Morrison | 2005/0228377 A1 | 10/2005 | Chao et al. |
| 6,736,817 | B2 | 5/2004 | Troxell | 2006/0058789 A1 | 3/2006 | Kim et al. |
| 6,752,807 | B2 | 6/2004 | Lin | 2006/0142759 A1 | 6/2006 | Arnin et al. |
| 6,761,721 | B2 | 7/2004 | Burgess et al. | 2006/0241757 A1 | 10/2006 | Anderson |
| 6,811,567 | B2 | 11/2004 | Reiley | 2007/0043356 A1 | 2/2007 | Timm et al. |
| 6,887,241 | B1 | 5/2005 | McBride et al. | 2007/0049936 A1 | 3/2007 | Colleran et al. |
| 6,958,066 | B2 | 10/2005 | Richelsoph et al. | 2007/0073396 A1 | 3/2007 | Arnin |
| 7,011,685 | B2 | 3/2006 | Arnin et al. | | | |
| 2002/0007183 | A1 | 1/2002 | Lee et al. | | | |
| 2002/0052603 | A1 | 5/2002 | Nichols | | | |

FOREIGN PATENT DOCUMENTS

| | | |
|---|---|---|
| DE | 3219575 | 12/1983 |
| DE | 3639810 | 5/1988 |
| DE | 4330837 | 3/1995 |
| EP | 0128058 | 12/1984 |
| EP | 0242708 | 10/1987 |
| EP | 0669109 | 2/1994 |
| EP | 0820722 | 1/1998 |
| EP | 0878170 | 11/1998 |
| EP | 0956829 | 11/1999 |
| EP | 1295566 | 3/2003 |
| FR | 2816195 | 10/1986 |
| FR | 2615095 | 11/1988 |
| FR | 2624720 | 6/1989 |
| FR | 2645427 | 10/1990 |
| FR | 2697743 | 5/1994 |
| FR | 2714590 | 7/1995 |
| FR | 2615095 | 11/1998 |
| FR | 2813782 | 3/2002 |
| FR | 2795622 | 1/2005 |
| GB | 167228 | 7/1921 |
| GB | 2173104 | 10/1986 |
| GB | 2208476 | 4/1989 |
| JP | 11-244299 | 9/1999 |
| JP | 11244299 | 9/1999 |
| JP | 2000-033091 | 2/2000 |
| SU | 286136 | 11/1970 |
| SU | 1823791 | 6/1993 |
| WO | WO-87/00160 | 1/1987 |
| WO | WO-90/04948 | 5/1990 |
| WO | WO-91/16020 | 10/1991 |
| WO | WO-95/13754 | 5/1995 |
| WO | WO-9909903 | 3/1999 |
| WO | WO-00/57801 | 10/2000 |
| WO | WO-00/59387 | 10/2000 |
| WO | WO-01/01872 | 1/2001 |
| WO | WO-01/24718 | 4/2001 |
| WO | 01/45576 | 6/2001 |
| WO | 0147425 | 7/2001 |

| | | | |
|---|---|---|---|
| 2002/0065557 | A1 | 5/2002 | Goble et al. |
| 2002/0072800 | A1 | 6/2002 | Goble et al. |
| 2002/0095154 | A1 | 7/2002 | Atkinson et al. |
| 2002/0111625 | A1 | 8/2002 | Richelsoph et al. |
| 2002/0123806 | A1 | 9/2002 | Reiley |
| 2002/0133155 | A1 | 9/2002 | Ferree |
| 2002/0138077 | A1 | 9/2002 | Ferree |
| 2002/0143330 | A1 | 10/2002 | Shluzas |
| 2002/0169448 | A1 | 11/2002 | Vanacker |
| 2003/0004572 | A1 | 1/2003 | Goble et al. |
| 2003/0018334 | A1 | 1/2003 | Richelsoph et al. |
| 2003/0023244 | A1 | 1/2003 | Richelsoph et al. |
| 2003/0028192 | A1 | 2/2003 | Schar et al. |
| 2003/0028250 | A1 | 2/2003 | Reiley et al. |
| 2003/0045874 | A1 | 3/2003 | Thomas |
| 2003/0055427 | A1 | 3/2003 | Graf |
| 2003/0083657 | A1 | 5/2003 | Drewry |
| 2003/0109880 | A1 | 6/2003 | Shirado et al. |
| 2003/0114853 | A1 | 6/2003 | Burgess et al. |
| 2003/0135277 | A1 | 7/2003 | Bryan et al. |
| 2003/0153912 | A1 | 8/2003 | Graf |
| 2003/0153917 | A1 | 8/2003 | Richelsoph et al. |
| 2003/0171749 | A1 | 9/2003 | Le Couedic et al. |
| 2003/0171750 | A1 | 9/2003 | Chin |
| 2003/0191470 | A1 | 10/2003 | Ritland |
| 2003/0191532 | A1 | 10/2003 | Goble et al. |
| 2003/0220642 | A1 | 11/2003 | Freudiger |
| 2003/0220643 | A1 | 11/2003 | Ferree |
| 2004/0002708 | A1 | 1/2004 | Ritland |
| 2004/0006342 | A1 | 1/2004 | Altarac et al. |
| 2004/0006391 | A1 | 1/2004 | Reiley |
| 2004/0039385 | A1 | 2/2004 | Mazda |
| 2004/0049188 | A1 | 3/2004 | Slivka et al. |
| 2004/0049189 | A1 | 3/2004 | Le Couedic et al. |
| 2004/0049190 | A1 | 3/2004 | Biedermann et al. |
| 2004/0049272 | A1 | 3/2004 | Reiley |
| 2004/0049273 | A1 | 3/2004 | Reiley |
| 2004/0049274 | A1 | 3/2004 | Reiley |

| WO | 02/17803 | 3/2002 |
| WO | WO-02/30307 | 4/2002 |
| WO | 02/43603 | 6/2002 |
| WO | 02/102259 | 12/2002 |
| WO | 03/007828 | 1/2003 |
| WO | 03/009737 | 2/2003 |
| WO | 2004/024011 | 3/2004 |
| WO | 2004/034916 | 4/2004 |

OTHER PUBLICATIONS

International Search Report issued for PCT/US06/31000; mailing date Mar. 20, 2008; 4 pages.
Asher, et al., "A Modular Spinal Rod Linkage System to Provide Rotational Stability", SPINE, vol. 13, No. 3, pp. 272-277, 1998.
"OvationTM Polyaxial System" by Osteotech, Inc., description downloaded from http://www.osteotech.com/prodpoly2.htm; pp. 1-6.
Carson et al., "Internal Forces and Moments in Transpecular Spine Instrumentation", SPINE, vol. 15, No. 9, pp. 893-901.
Martin H. Krag, "Biomechanics of Thorocolumbar Spinal Fixation," SPINE, vol. 16, No. 3, Supplement, pp. S84-S99 (1991).
Lim, et al., "Biomechanics of Transfixation in Pedicle Screw Instrumentation", SPINE, vol. 21, No. 19, pp. 2224-2229, 1996.
Betz, Randall R. et al., DePuy AcroMed Brochure, "Fronterior Anterior Deformity System," Surgical Technique, 21 pages, Aug. 2002.
DePuy AcroMed, "CrossOver CrossConnector" brochure, Apr. 2003.
Dick et al., "Mechanical Evaluation of Cross-Link Designs in Rigid Pedicle Screw Systems", SPINE, vol. 22, No. 4, pp. 370-375, 1997.
Kaneda, Kiyoshi et al., DePuy AcroMed Brochure "Kaneda SR Anterior Spinal System," Surgical Technique, pp. 1-11, 1999.
Office Action dated Apr. 20, 2009 issued in U.S. Appl. No. 10/813,904.

* cited by examiner

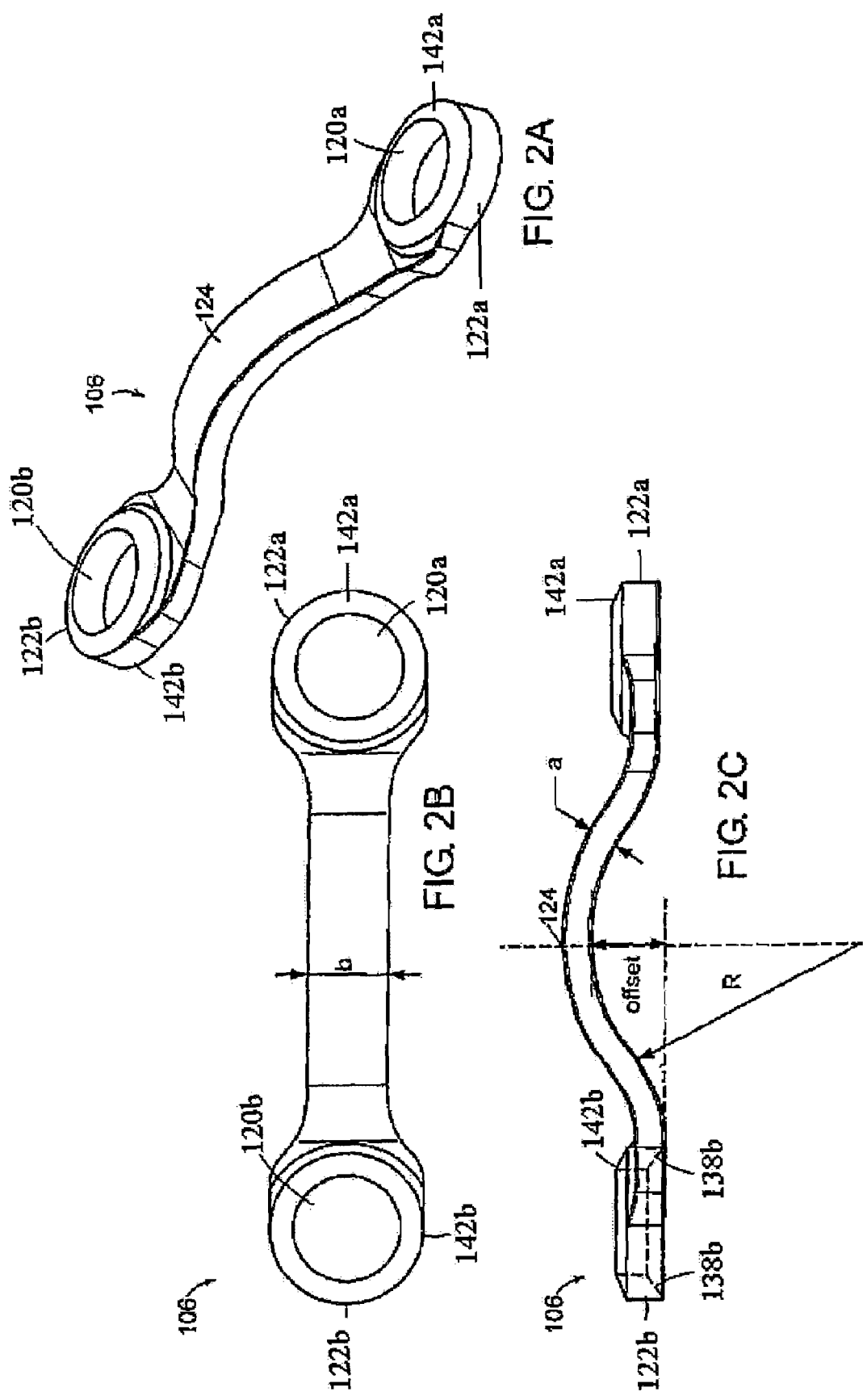

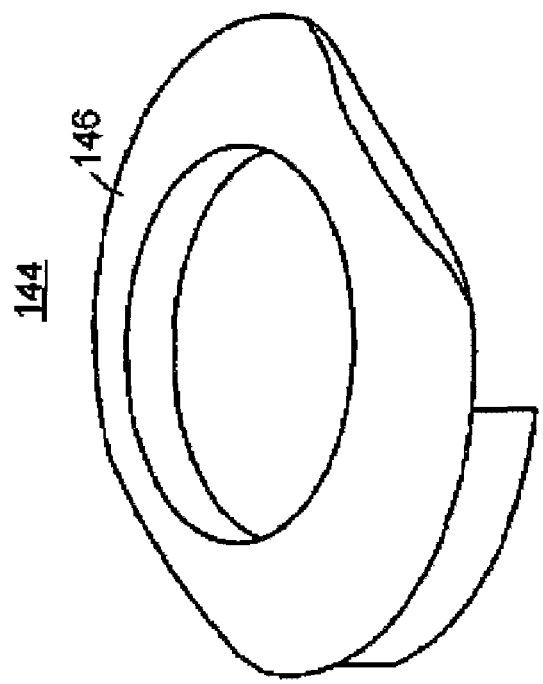
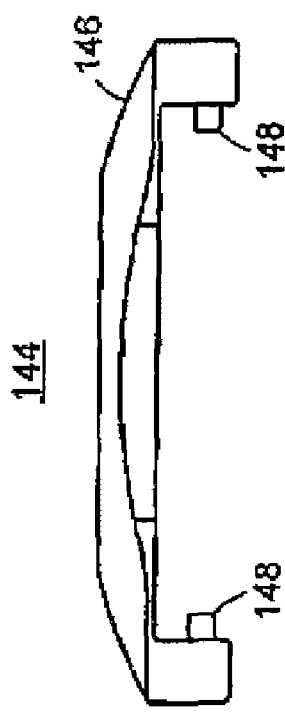
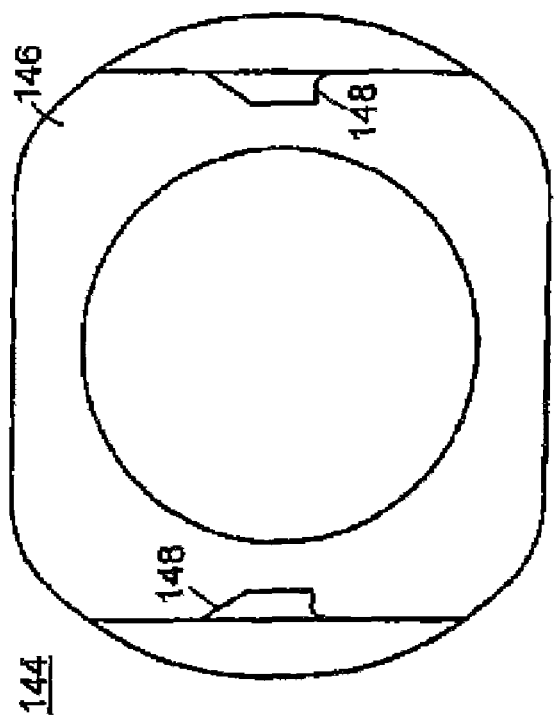
FIG. 11A
FIG. 11B
FIG. 11C

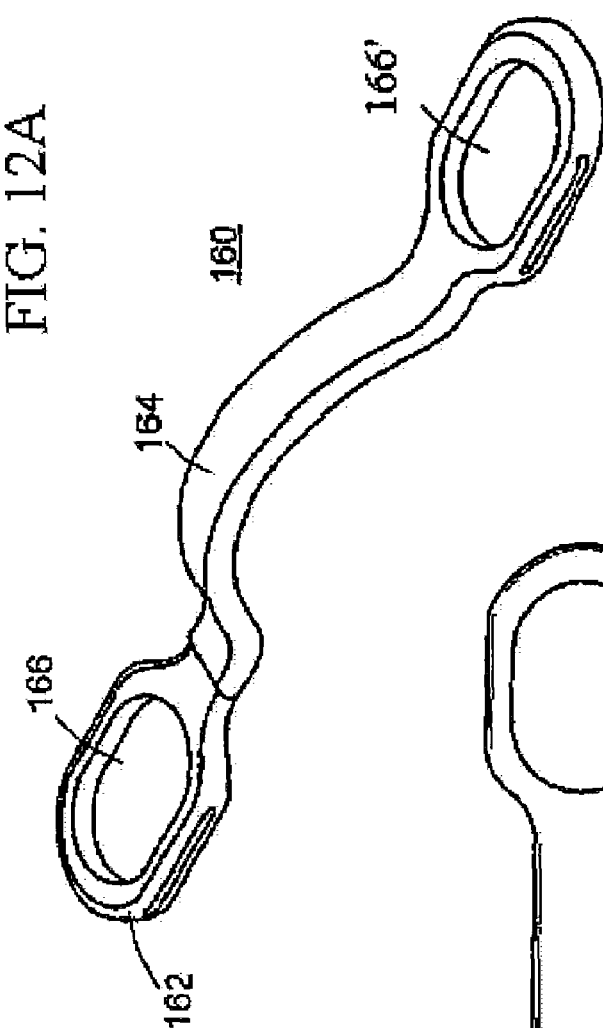
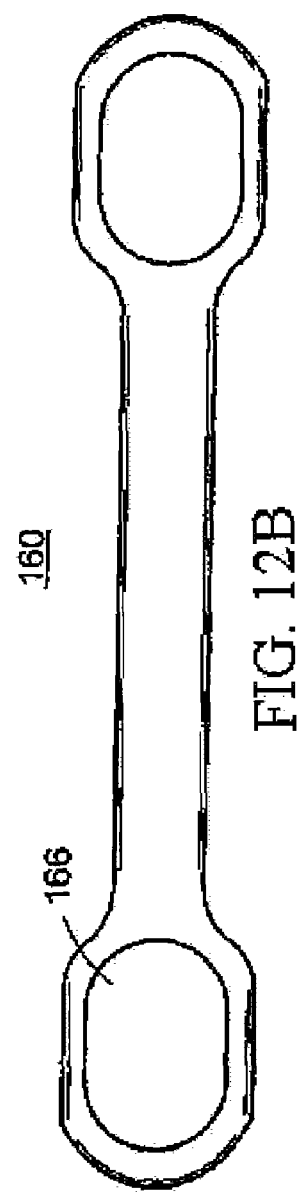
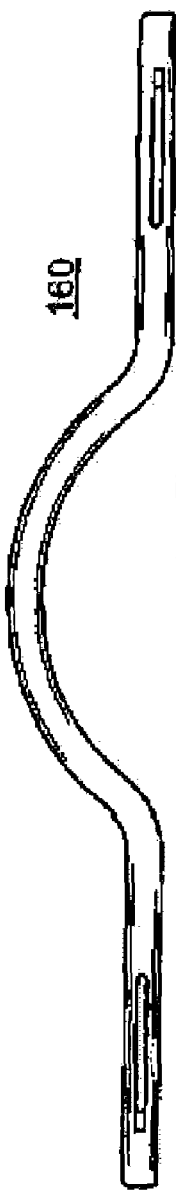
FIG. 12A
FIG. 12B
FIG. 12C

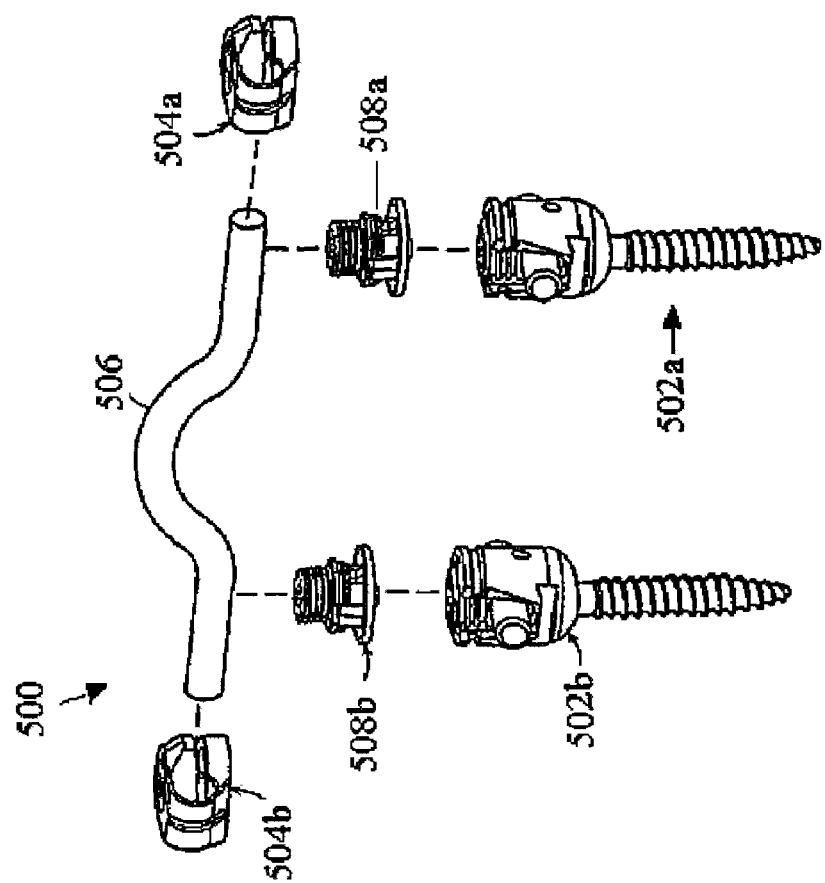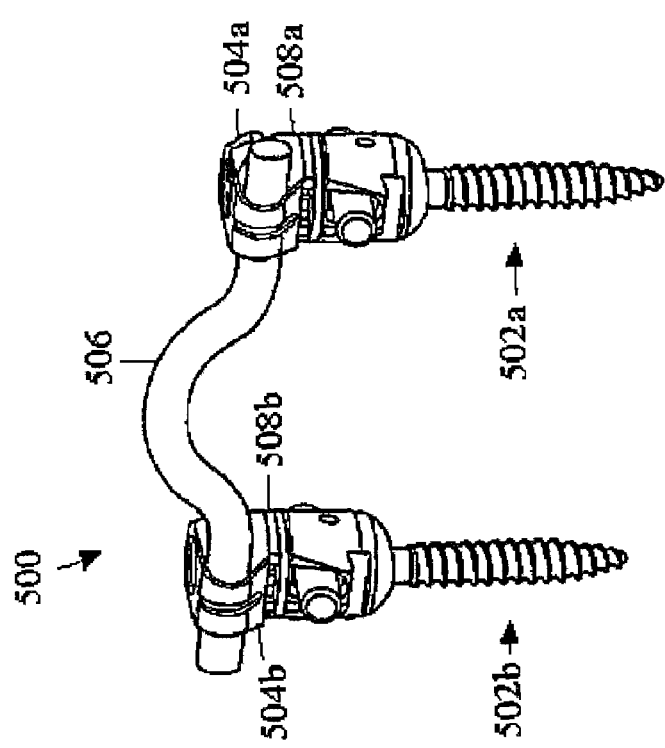
FIG. 15B
FIG. 15A

ROD ATTACHMENT FOR HEAD TO HEAD CROSS CONNECTOR

CROSS REFERENCE TO RELATED APPLICATIONS

This application is a continuation-in-part of U.S. patent application Ser. No. 10/813,904 filed on Mar. 31, 2004 and entitled "Head-To-Head Connector Spinal Fixation System," which is hereby incorporated by reference in its entirety.

BACKGROUND

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. Alternatively, two rods can be disposed on the lateral or anterior surface of the vertebral body in a substantially parallel relationship. The fixation rods can have a predetermined contour that has been designed according to the properties of the target implantation site, and once installed, the rods hold the vertebrae in a desired spatial relationship, either until desired healing or spinal fusion has taken place, or for some longer period of time.

Spinal cross connectors are often used in conjunction with spinal fixation devices to provide additional stability to the devices. For example, it has been found that when a pair of spinal rods are fastened in parallel on either side of the spinous process, the assembly can be significantly strengthened by using a cross connector to bridge the pair of spinal rods. The connectors are typically in the form of a rod having a clamp formed on each end thereof for mating with a spinal rod.

While current spinal cross connectors have proven effective, difficulties have been encountered in mounting the cross connectors, and maintaining them in a desired position and orientation with respect to the spinal rod, or other spinal fixation device to which they are attached. In particular, the clamp assemblies often consist of several parts which make surgical application tedious, and which can also increase the manufacturing costs. Since the cross connector is often applied as the last step in a lengthy surgical procedure, ease of application is paramount. Fixation of the cross connector to spinal rods can also be difficult where the rods are not parallel to one another, or they are diverging/converging with respect to one another, or where other spinal fixation devices interfere with proper placement.

Accordingly, there exists a need for an improved spinal cross connector that can be easily installed and that securely mates to and connects spinal fixation devices.

BRIEF SUMMARY

The present invention relates to spinal fixation systems and method for stabilizing vertebrae in a patient's spine. In an exemplary embodiment, methods and device are provided for coupling one or more bone anchors, such as hooks, screws, etc., and/or one or more spinal fixation elements, such as spinal rods, cables, plates, etc. In certain exemplary embodiments, a cross connector is provided for connecting and stabilizing two bone anchors, a bone anchor and a spinal fixation element, or a bone anchor and bone.

In one exemplary embodiment, a spinal fixation system is provided having a cross connector that is configured to span between opposed lateral sides of a vertebra and having first and second ends. A coupling member is configured to mate to the first end of the cross connector and it can include a rod-receiving recess formed therein for coupling to a spinal rod. The coupling member is preferably configured to couple to a spinal rod without anchoring to bone. The system can also include a bone anchor having a shaft for engaging bone and a head configured to mate to the second end of the connector and having a rod-receiving recess formed therein for coupling to a spinal rod.

The coupling member can have a variety of configurations, and in one embodiment it can have a side-loading rod-receiving recess, i.e., the coupling member is loaded onto a spinal rod from the side. For example, the rod-receiving recess formed in the coupling member can be defined by a top wall, a bottom wall, and a side wall connecting the top and bottom walls. In an exemplary embodiment, the top wall includes a thru-bore formed therein for receiving a fastening element adapted to mate the coupling member to the cross connector. The system can also include a fastening element that is adapted to extend through an opening formed in the first end of the cross connector and to extend into the thru-bore formed in the top wall of the coupling member for mating the coupling member to the cross connector. The fastening element can also extend into the rod-receiving recess to lock a spinal rod disposed therein to the coupling member.

In another embodiment, the coupling member can have a top-loading rod-receiving recess, i.e., the coupling member is loaded onto a spinal rod from the top. For example, the rod-receiving recess formed in the coupling member can be defined by a top wall and first and second side walls extending from opposed sides of the top wall. In an exemplary embodiment, the top wall includes a thru-bore formed therein for receiving a fastening element adapted to mate the coupling member to the cross connector.

In other embodiments, the coupling member can include features to facilitate locking of a spinal rod therein. For example, the coupling member can include a locking arm extending into the rod-receiving recess and adapted to extend around at least a portion of a rod disposed within the rod-receiving recess. In an exemplary embodiment, the locking arm extends through one of the first and second side walls of the coupling member. A fastening element can extend through an opening formed in the first end of the cross connector and into the thru-bore formed in the top wall of the coupling member to abut against the locking arm and thereby lock a rod within the rod-receiving recess of the cross connector.

In other embodiments, the coupling member can include at least one movable member adapted to move in response to a force applied thereto by the fastening element to engage a rod disposed within the rod-receiving recess. The movable member can be one or more pivoting or sliding wedges. For example, the coupling member can include a wedge disposed therein and adapted to be engaged by the fastening element such that the wedge moves to engage a rod disposed within the rod receiving recess of the coupling member.

Exemplary methods for spinal stabilization are also provided. In one embodiment, the method can include coupling a first end of a cross connector to a head of a bone anchor to anchor the first end of the cross connector to a first vertebra, the bone anchor having a first spinal rod extending therethrough, and coupling a second end of the cross connector to a second spinal rod without anchoring the second end of the cross connector to the first vertebra. In an exemplary embodiment, the second spinal rod is positioned within a rod receiving recess of a coupling member, and a fastening element is inserted through the second end of the cross connector and into an opening formed in the coupling member to lock the spinal rod, coupling member, and cross connector to one another. Depending on the configuration of the coupling member, the spinal rod can be side-loaded into a rod-receiving recess formed in a sidewall of the coupling member, or it can be bottom-loaded into a rod-receiving recess formed in a bottom wall of the coupling member. The fastening element can then be inserted into an opening formed in a top wall of the coupling member to lock the rod therein and to mate the coupling member to the cross connector.

BRIEF DESCRIPTION OF THE DRAWINGS

The invention will be more fully understood from the following detailed description taken in conjunction with the accompanying drawings, in which:

FIG. 2A is a perspective view of the connecting plate of the spinal fixation system shown in FIGS. 1A and 1B;

FIG. 2B is a top view of the connecting plate shown in FIG. 2A;

FIG. 2C is a side view of the connecting plate shown in FIG. 2A;

FIG. 11A is a perspective view of the floating washer of the spinal fixation system shown in FIG. 10;

FIG. 11B is a side view of the floating washer shown in FIG. 11A;

FIG. 11C is a top view of the floating washer shown in FIG. 11A;

FIG. 12A is a perspective view of one embodiment of a connecting plate;

FIG. 12B is a top view of the connecting plate shown in FIG. 12A;

FIG. 12C is a side view of the connecting plate shown in FIG. 12A;

FIG. 15A is a perspective view of yet another embodiment of a spinal fixation system;

FIG. 15B is an exploded view of the spinal fixation system shown in FIG. 15A;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, various spinal fixation systems are provided for aligning and/or fixing a desired relationship between adjacent vertebral bodies. In one exemplary embodiment, the spinal fixation system includes one or more bone anchors, such as bone screws, one or more spinal fixation elements, such as spinal rods, plate, or cables, and one or more connecting plates. In use, one or more bone anchors can be implanted in one or more adjacent vertebrae, for example in the pedicle, lamina, or lateral mass of a vertebra, and the spinal fixation element(s) can extend generally along the axis of the spine between one or more bone anchors. The connecting plate(s) can couple to and extend between two bone anchors, or a bone anchor and a spinal fixation element, positioned on opposed sides of the spine, thus providing additional stability to the assembly. In one embodiment, the connecting plate can protect the spinal cord after a full or partial laminectomy.

Figure 1A:
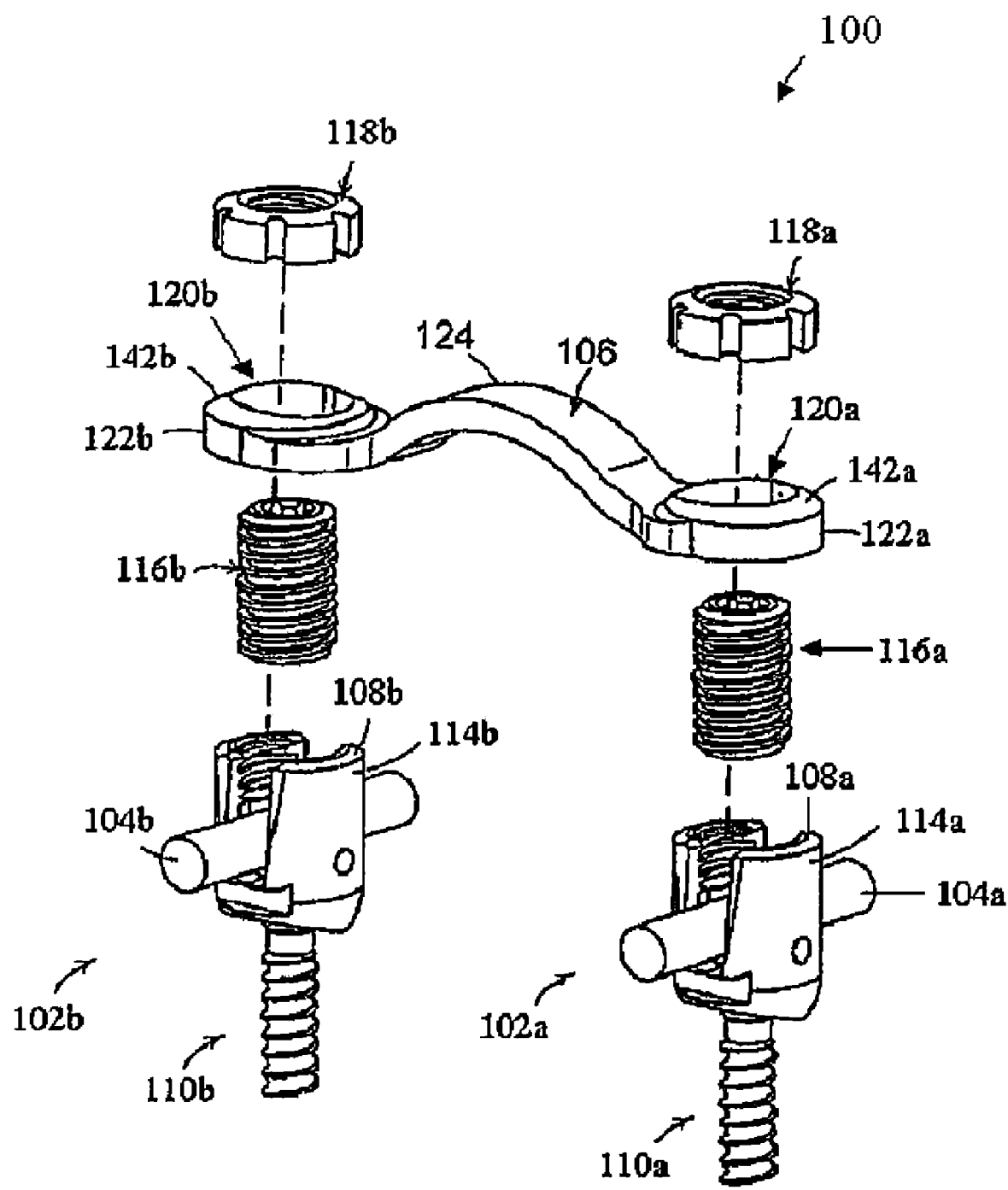
FIG. 1A is an exploded perspective view of one embodiment of a spinal fixation system.
Figure 1B:
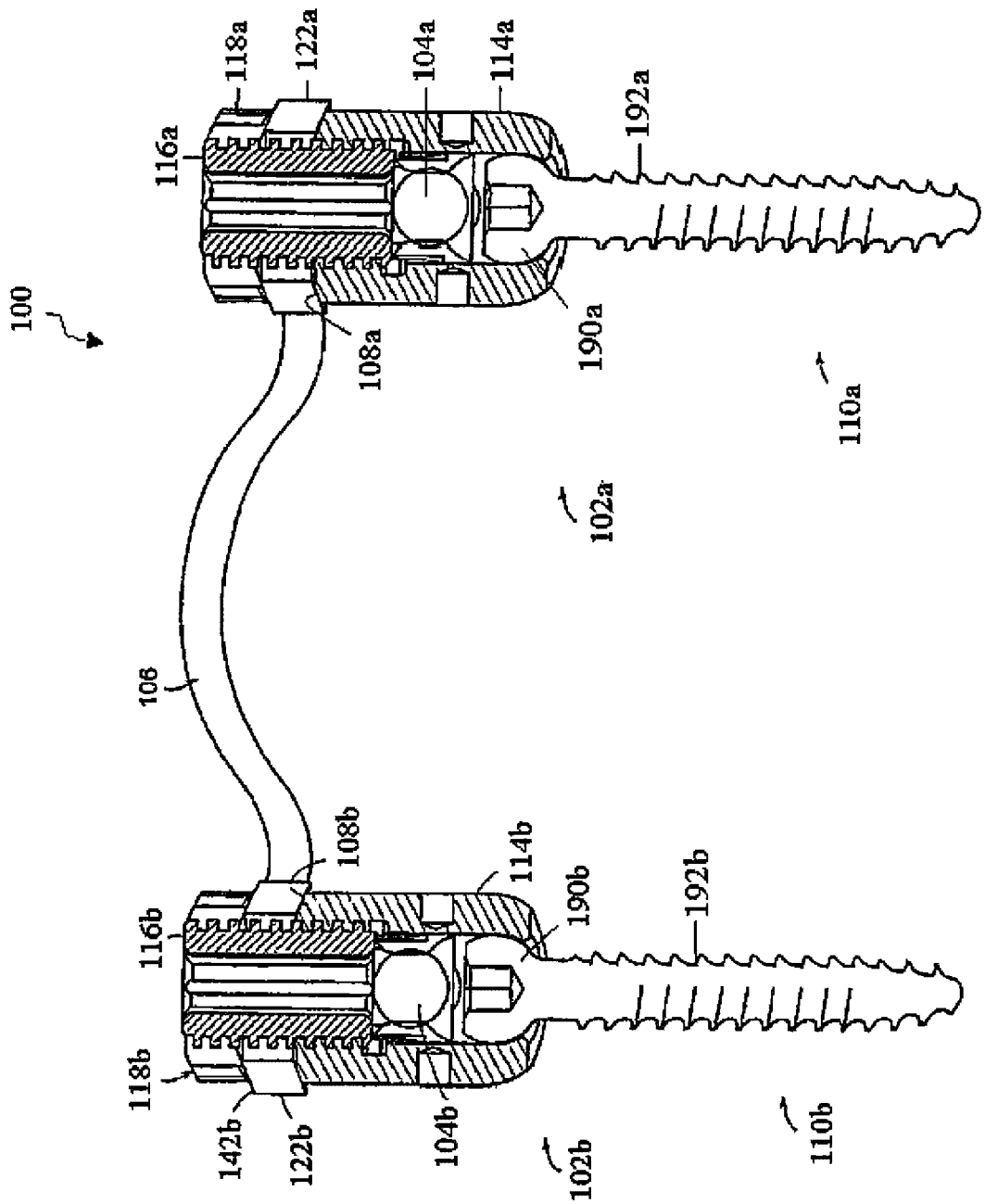
FIG. 1B is a cross-sectional view of the spinal fixation system shown in FIG. 1A in an assembled configuration.

FIGS. 1A and 1B illustrate one exemplary embodiment of a spinal fixation system 100 having a connecting plate that is adapted to extend between two bone anchors. As shown, the system 100 generally includes first and second bone anchors in the form of bone screws 102a, 102b, first and second spinal fixation elements in the form of spinal rods 104a, 104b that are connected to the first and second bone anchors 102a, 102b, respectively, and a connecting plate 106 extending between the first and second bone anchors 102a, 102b. While the rods 104a, 104b and the connecting plate 106 can be mated to the bone anchors 102a, 102b using a variety of techniques, in the illustrated embodiment the spinal fixation system 100 includes first and second set screws 116a, 116b that threadably engage a rod receiving portion 114a, 114b of each bone anchor 102a, 102b to mate the spinal fixation rods 104a, 104b to the bone anchors 102a, 102b, and first and second caps 118a, 118b that threadably engage the set screws 116a, 116b to fix the connecting plate 106 to the rod-receiving portion 114a, 114b of each bone anchor 102a, 102b. In use, the bone anchors 102a, 102b can be implanted in opposed lateral sides of a vertebra, and the spinal rods 104a, 104b can extend through the bone anchors 102a, 102b to couple the bone anchors 102a, 102b to one or more spinal anchors implanted in adjacent vertebrae. The connecting plate 106 can be mated to the first and second bone anchors 102a, 102b using the set screws 116a, 116b and the caps 118a, 118b, thereby providing additional stability to the spinal stabilization system 100.

Each bone anchor 102a, 102b can have a variety of configurations, and various bone anchors known in the art may be used with the spinal stabilization system 100, including, for example, monoaxial bone screws, polyaxial bone screws, bolts, hooks, or any other implant or combination of implants designed to engage bone and connect to a spinal fixation element, such as a spinal rod 104a, 104b. In the illustrated embodiment, the bone anchors 102a, 102b are polyaxial bone screws, each having a distal portion 110a, 110b that is adapted to be disposed within bone, and rod receiving portion 114a, 114b that is adapted to seat a spinal rod 104a, 104b, or other spinal fixation element therein. The rod receiving portion 114a, 114b of each bone anchor 102a, 102b can include a proximal bearing surface 108a, 108b that has a shape or configuration that is adapted to match the shape or configuration of the connecting plate 106, as will be described in more detail below. The distal portion 110a, 110b of each bone anchor 102a, 102b can include a threaded shaft 192a, 192b and head 190a, 190b formed thereon and adapted to sit within and pivot related to the rod receiving portion 114a, 114b. As previously indicated, a person skilled in the art will appreciate that a variety of bone anchors known in the art can be used with the spinal fixation system 100.

The connecting plate 106 of the system 100 can also have a variety of configurations, but it is preferably adapted to span laterally across a vertebra such that the connecting plate 106 can extend between and couple to the bone anchors 102a, 102b implanted in opposed lateral sides of a vertebra. The connecting plate 106 is shown in more detail in FIGS. 2A-2C, and as shown the connecting plate 106 has a generally elongate shape with a spanning portion 124 having opposed ends 122a, 112b.

The spanning portion 124 can have a variety of configurations, including a planar configuration, or an arcuate shape as shown. In one exemplary embodiment, the spanning portion 124 can have a radius of curvature in a range of between about 5 mm and 15 mm, and more preferably about 8 mm and 12 mm. The spanning portion 124 of the connecting plate 106 can also vary with respect to thickness a, as indicated in FIG. 2C. In an exemplary embodiment, the thickness a is less that a width b of the plate, as indicated in FIG. 2B. Such a configuration allows for intraoperative contouring of the plate to accommodate patient anatomy yet also provides geometric stiffness to impart torsional rigidity to the plate and spinal construct. As is further shown in FIGS. 2A-2C, the spanning portion 124 can also be offset from a plane defined by the ends 122a, 122b of the connecting plate 106. For example, in one exemplary embodiment the spanning portion 124 can be offset by at least about 3 mm from a plane defined by the end 122a, 112b of the connecting plate 106, and more preferably the spanning portion 124 can be offset by between about 5 mm to 10 mm from a plane defined by the ends 122a, 122b of the connecting plate 106.

As is further shown, the connecting plate 106 can also include an opening 120a, 120b formed in each end 122a, 122b thereof for receiving a set screw 116a, 116b that mates to the rod-receiving portion 114a, 114b of each bone screw 102a, 102b. The openings 120a, 120b defined by the connecting plate 106 may circular, elliptical, polygonal, or have any other shape, as will be discussed in more detail below with respect to FIGS. 12A-14C. In operation, each end 122a, 122b is adapted to be positioned on top of the rod-receiving portion 114a, 114b of each bone screw 102a, 102b, as shown in FIG. 1B. The ends 122a, 122b and the rod-receiving portion 114a, 114b of each bone screw 102a, 102b can thus include bearing surfaces that are shaped to facilitate mating of the components, as will be discussed in more detail below.

Figure 3A:
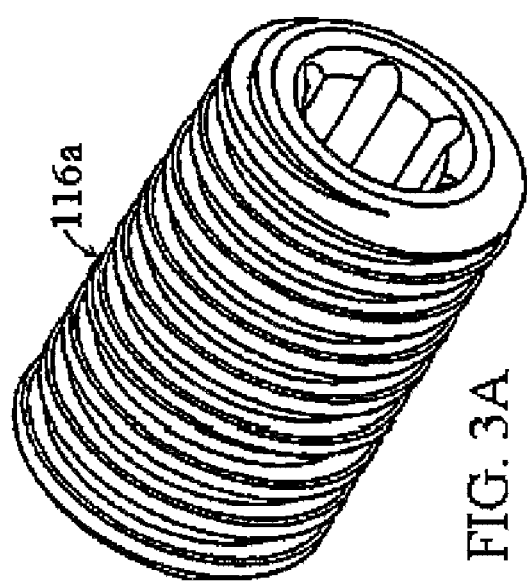
FIG. 3A is a perspective view of a set screw of the spinal fixation system shown in FIGS. 1A and 1B.
Figure 3B:
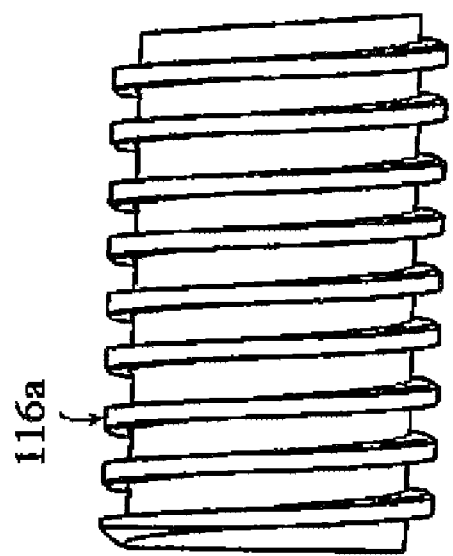
FIG. 3B is a side view of the set screw shown in FIG. 3A.
Figure 3C:
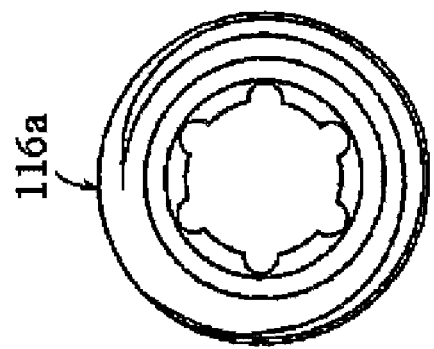
FIG. 3C is a top view of the set screw shown in FIG. 3A.

As previously explained, the device 100 can also include a closure mechanism, such as a set screw 116a, 116b for mating the rods 104a, 104b to the bone anchors 102a, 102b. One of the sets screws, e.g., set screw 116a, is shown in more detail in FIGS. 3A-3B. As shown, the set screw 116a has a generally cylindrical shape with threads formed therearound for mating with corresponding threads formed within the rod-receiving portion 114a of the bone anchor 102a. In use, the set screw 116a can be threaded into the bone anchor 102a to lock the rod 104a within the rod receiving portion 114a of the anchor 102a, as shown in FIG. 1B. A person skilled in the art will appreciate that a variety of techniques can be used to mate the set screw 116a to the bone anchor 102a including, for example, a twist-lock mechanism or other non-threaded closure mechanism.

Figure 4A:
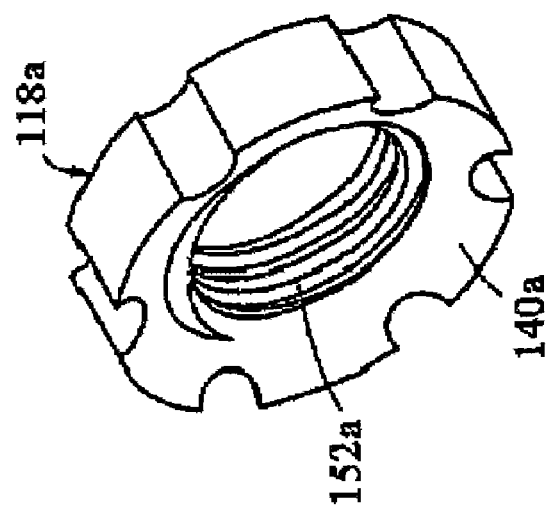
FIG. 4A is a perspective view of the cap of the spinal fixation system shown in FIGS. 1A and 1B.
Figure 4B:
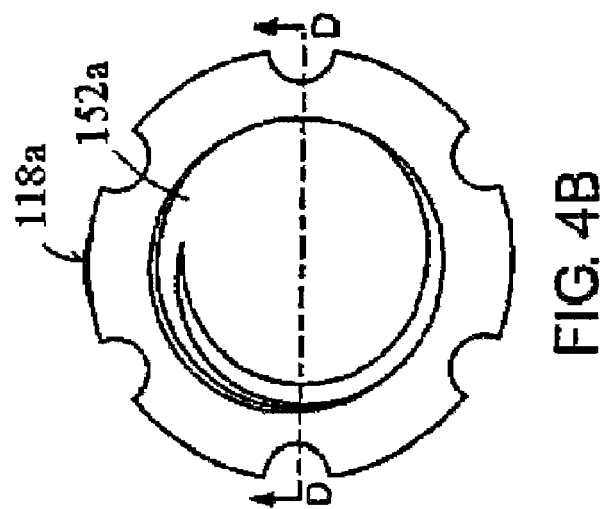
FIG. 4B is a top view of the cap shown in FIG. 4A.
Figure 4C:
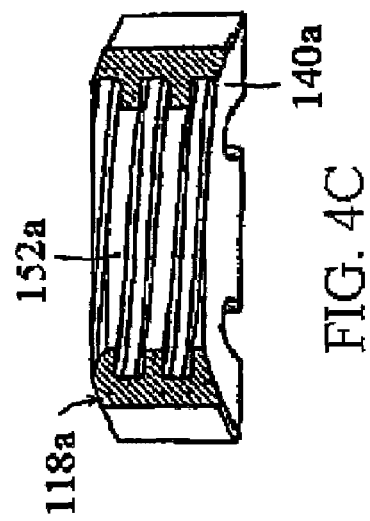
FIG. 4C is a side view of the cap shown in FIG. 4A.

The device 100 can also include one or more fastening elements for mating the connecting plate 106 to one or more bone anchors 102a, 102b. In an exemplary embodiment, the spinal fixation system 100 includes a locking nut or cap 118a, 118b that mates to each set screw 116a, 116b, which in turn are mated to the bone anchors 102a, 102b. Each cap 118a, 118b can have a variety of configurations. FIGS. 4A-4C illustrate cap 118a in more detail. As shown, the cap 118a has a generally circular shape with an opening formed therethrough and adapted to receive the set screw 116a. The opening can include threads 152a, or other mating features, formed therein and adapted to mate with corresponding threads, or other mating features, formed on the set screw 116a. In use, as previously shown in FIG. 1B, the caps 118a, 118b are mated to the set screw 116a after the opening 120a, 120b in the ends of the connecting plate 106 are positioned over the set screws 116a, 116b. An inferior bearing surface 140a, 140b of each cap 118a, 118b will thus engage the ends 122a, 112b of the connecting plate 106, locking the connecting plate 106 to the bone anchors 102a, 102b.

Figure 5A:
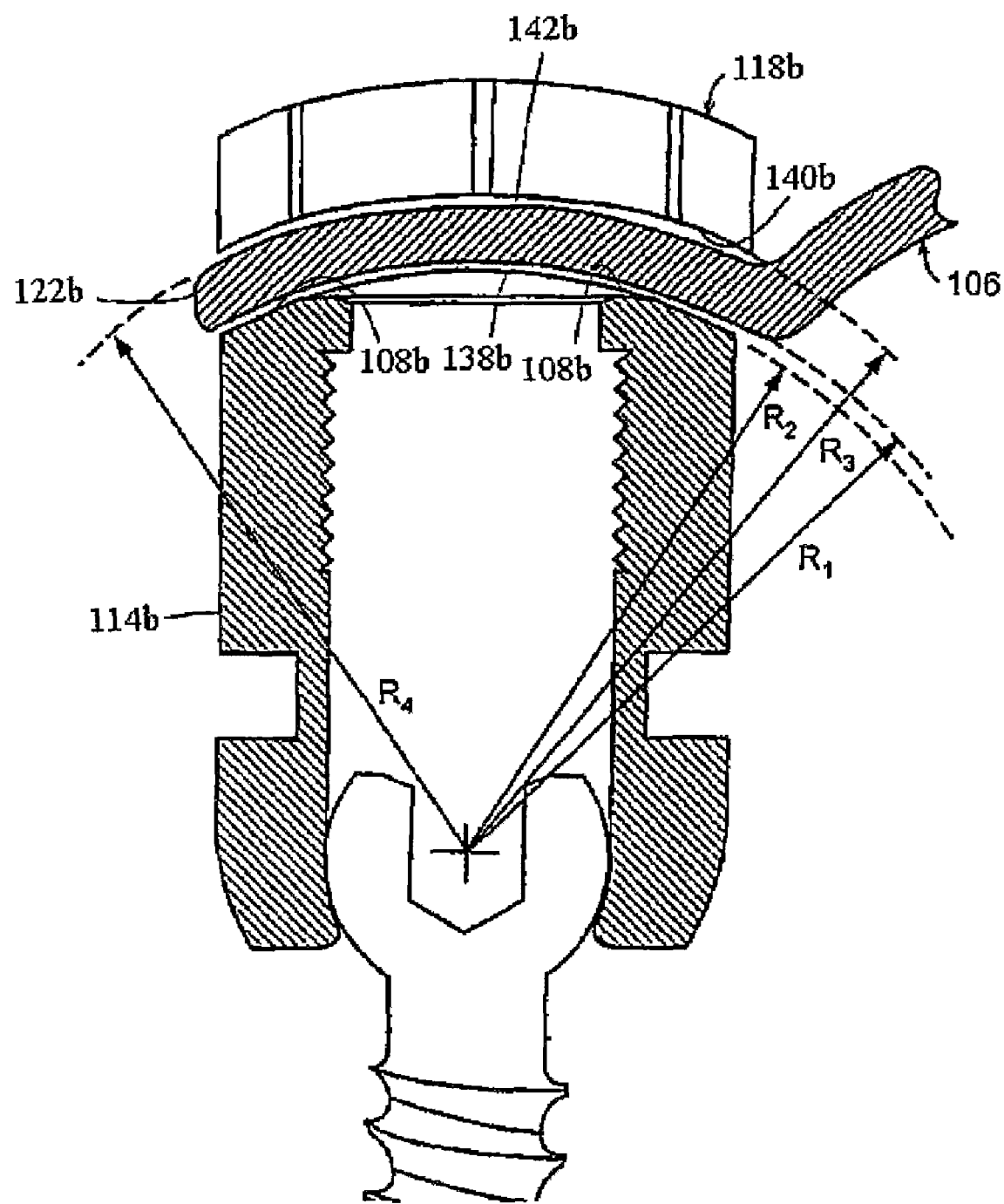
FIG. 5A is a cross-sectional, partially assembled view of the first end of the spinal fixation system shown in FIGS. 1A and 1B, showing domed bearing surfaces.
Figure 5B:
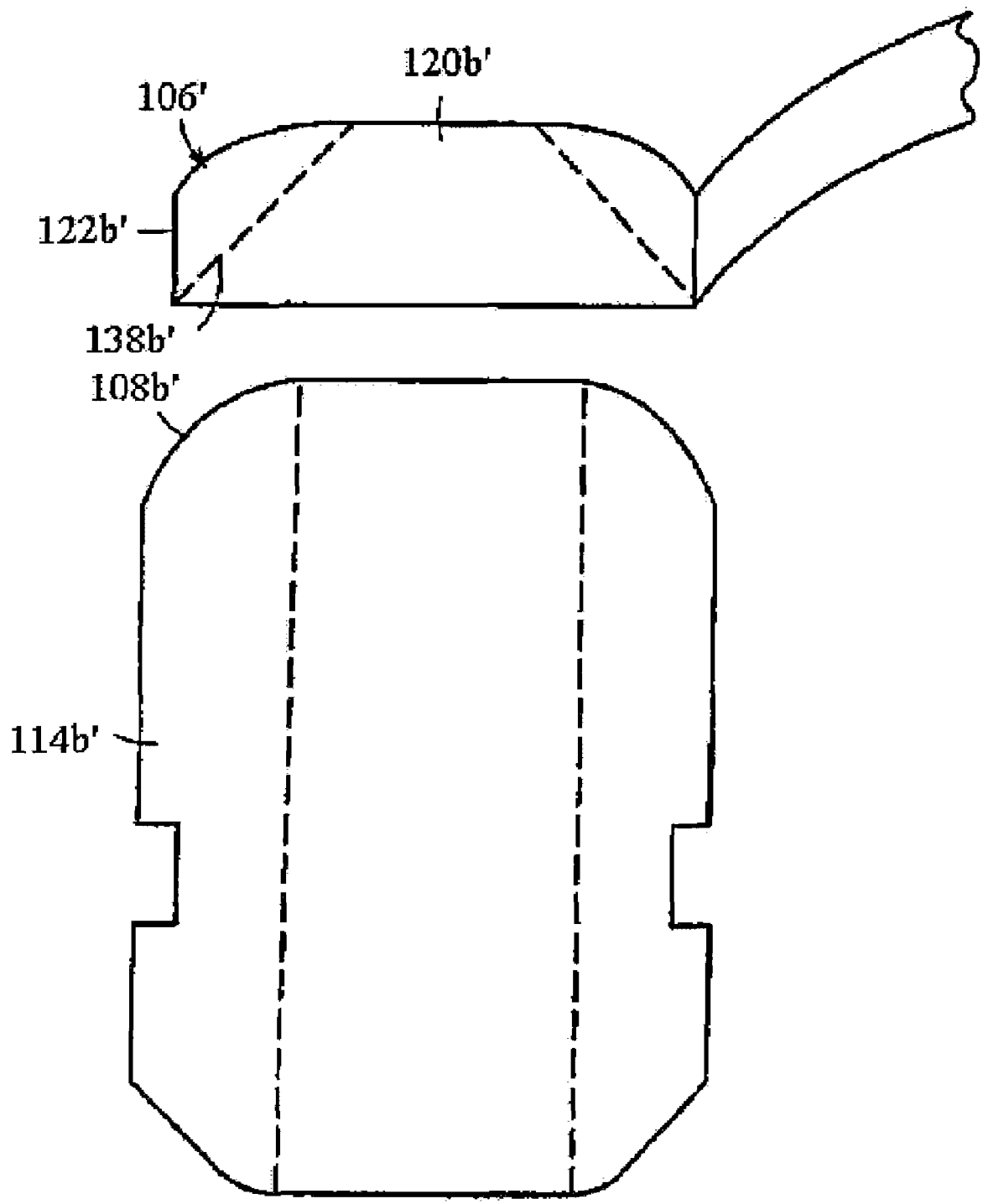
FIG. 5B is a cross-sectional view of another embodiment of a partially assembled end portion of a spinal fixation system having bearing surfaces.

As previously indicated, the rod-receiving portion 114a, 114b of each bone screw 102a, 102b and the ends 122a, 112b of the connecting plate 106, as well as the caps 118a, 118b, can each have bearing surfaces that are shaped to facilitate mating of the components, and in particular to facilitate locking of the components in a fixed position relative to one another. For example, as shown in FIG. 2C, the connecting plate 106 can have an inferior bearing surface 138b that is conical or spherical. A proximal surface 108b of the bone anchor 102b that mates with the connecting plate 106 can have a corresponding spherical or conical shape that bears against the inferior bearing surface 138b on the connecting plate 106. In other embodiments, the bearing surface can have different shapes. For example, FIG. 5B illustrates a connecting plate 106' having an inferior bearing surface 138b' that is conical while the bearing surface 108b' on the rod-receiving portion 114b' of the bone anchor is spherical.

Each cap 118a, 118b can also have a bearing surface that is shaped to match a corresponding bearing surface formed on a superior bearing surface 142a, 142b of the connecting plate 106. For example, FIGS. 4A and 4C illustrate cap 118a having a distal bearing surface 140 that is concave to mate with a corresponding convex bearing surface formed on the superior bearing surface 142a, 142b of the connecting plate 106.

In other embodiments, the bearing surfaces may be spherical, convex, concave, flat, variations or combinations thereof, or they may have any other shape sufficient to facilitate coupling of the plate to the bone anchor.

The radius of curvature of the bearing surfaces can also vary. As shown in FIG. 5A, the spherical superior surface 108b of the rod receiving portion 114b can have a radius of curvature R1 that extends from the point about which the bone screw portion pivots. The bearing surface 140b of cap 118b can have a radius of curvature R4 that extends from the point about which the bone screw portion pivots. The inferior and superior bearing surfaces 138b, 142b of the connecting plate 106 can also have radii of curvature R2 and R3 that extends from the point about which the bone screw portion pivots. In other embodiments, the radii may extend from a point distinct from the pivot point of the bone screw. In certain exemplary embodiments, each of the radii R1, R2, R3 and R4 can be in a range between about 5 mm and 15 mm.

Figure 6B:
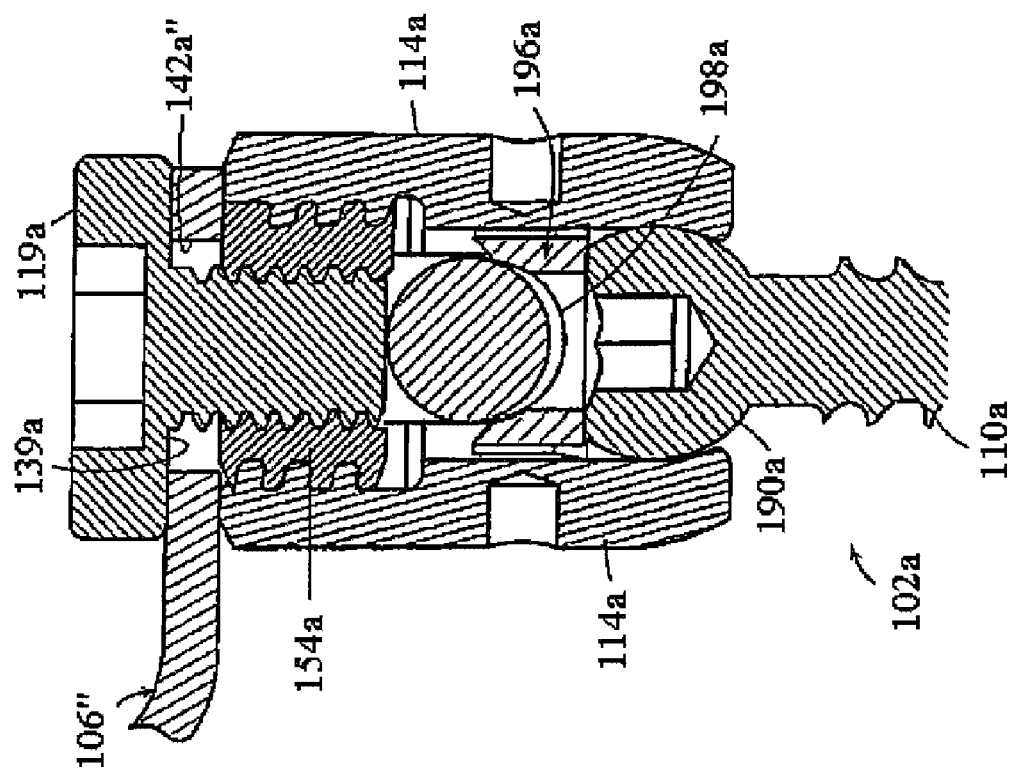
FIG. 6B is a cross-sectional view of an end portion of yet another embodiment of a spinal stabilization system.
Figure 6A:
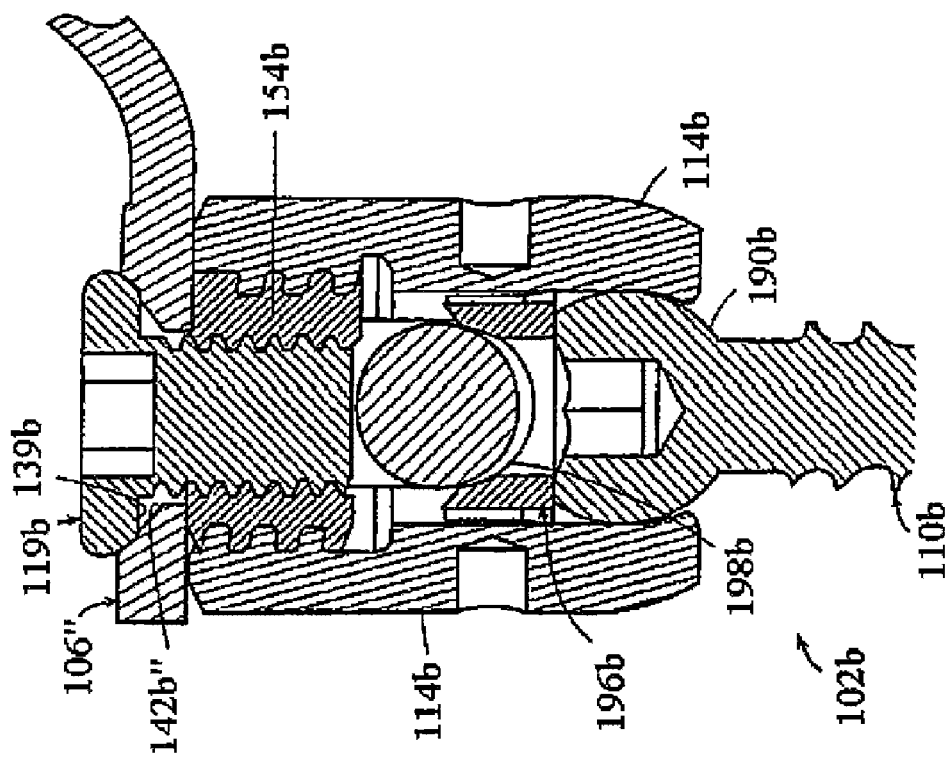
FIG. 6A is a cross-sectional view of an end portion of another embodiment of a spinal stabilization system.
Figure 7A:
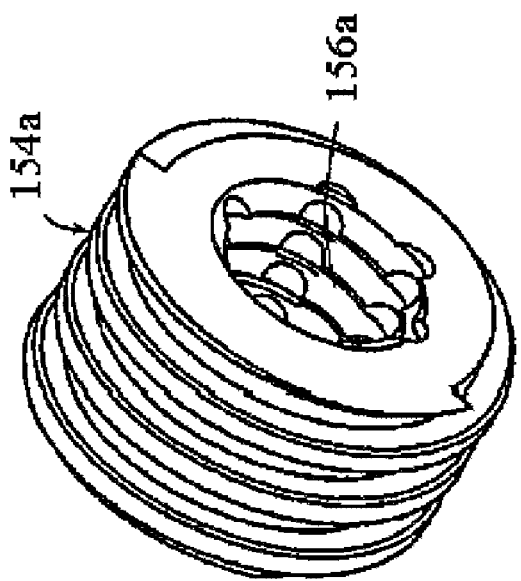
FIG. 7A is a perspective view of the set screw of the spinal stabilization system shown in FIG. 6B.
Figure 7D:
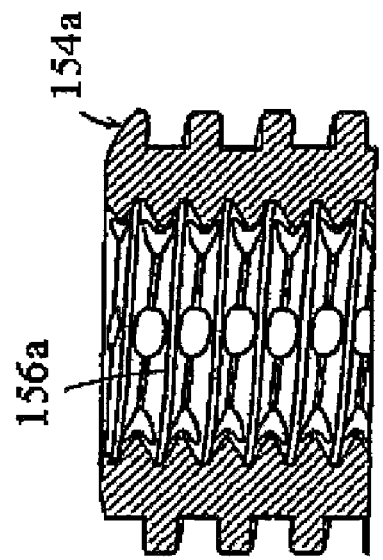
FIG. 7D is a cross-section view of the set screw shown in FIG. 7A.
Figure 7C:
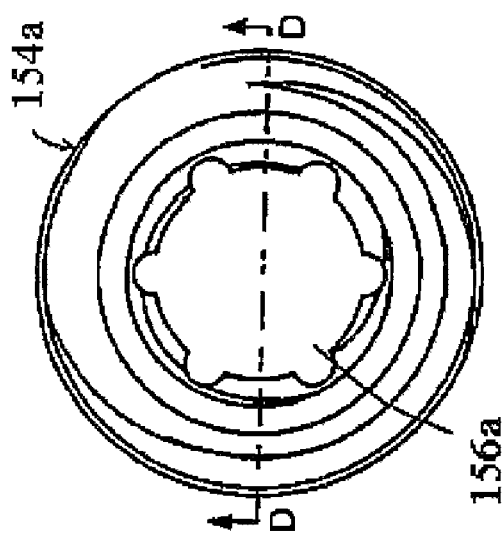
FIG. 7C is a top view of the set screw shown in FIG. 7A.
Figure 7B:
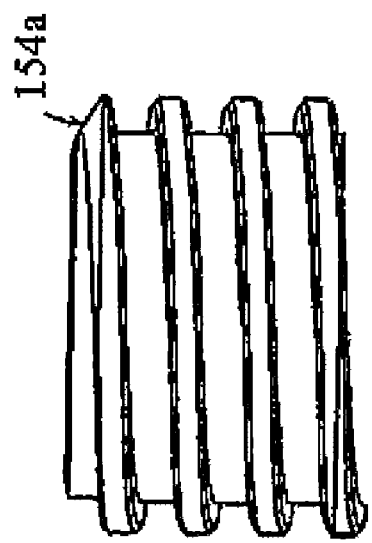
FIG. 7B is a side view of the set screw shown in FIG. 7A.
Figure 8A:
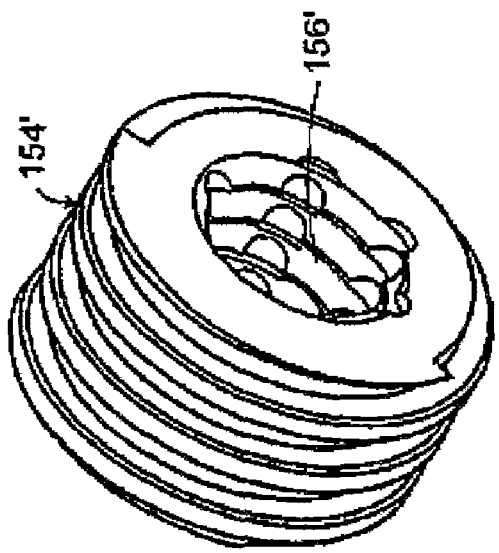
FIG. 8A is a perspective view of yet another embodiment of a set screw.
Figure 8D:
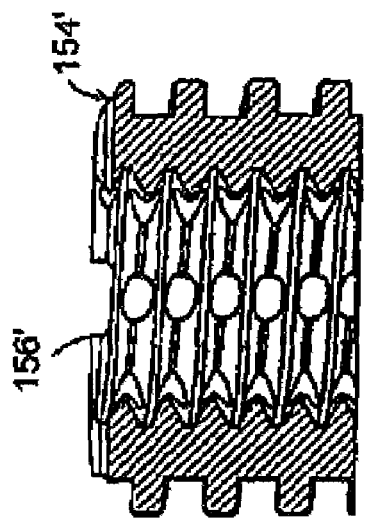
FIG. 8D is a cross-section view of the set screw shown in FIG. 8A.
Figure 8C:
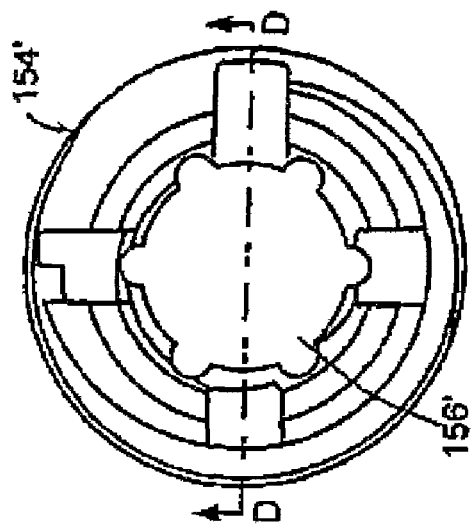
FIG. 8C is a top view of the set screw shown in FIG. 8A.
Figure 8B:
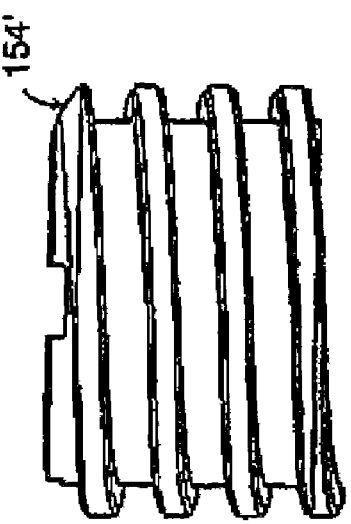
FIG. 8B is a side view of the set screw shown in FIG. 8A.

FIGS. 6A and 6B illustrate another embodiment of a spinal fixation system. In this embodiment, each bone anchor 102a, 102b includes a compression member 196a, 196b disposed within the rod-receiving portion 114a, 114b and that defines a rod seat 198a, 198b adjacent to the head 190a, 190b of the bone screw portion 110a, 110b. During operation of the spinal fixation system 100, the compression member 196a, 196b is disposed between the rod 104a, 104b and the head 190a, 190b of each bone anchor portion 110a, 110b.

As is further shown in FIGS. 6A and 6B, the cap 119a, 119b used to lock the connecting plate 106" has a threaded post that extends into and mates with corresponding threads formed in the set screw 154a, 154b mated to each bone anchor 102a, 102b. Set screw 154a is shown in more detail in FIGS. 7A-7D, and as shown the set screw 154a has a threaded bore 156a for mating with cap 119b. The set screw 154a also has a length that is less than a length of the set screws 116a, 116b illustrated in FIGS. 1A and 1B. An alternative embodiment of a set screw 154' having a threaded bore 156' for mating with cap 119a, 119b is shown in FIGS. 8A-8D.

Figure 9:
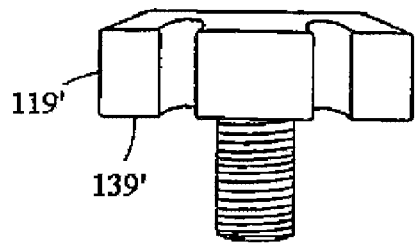
FIG. 9 is a cross-sectional view of another embodiment of a cap having a threaded post extending therefrom.

FIGS. 6A and 6B also illustrate various embodiments of bearing surfaces on the various components. For example, in FIG. 6A the inferior bearing surface 139b on the cap 119b is flat and it is received with a conical or concave bearing surface 142b" formed in the connecting plate 106". FIG. 6B also illustrates a cap 119a having a flat bearing surface 139a, however the cap 119a rests against the superior surface of the connecting plate 106". Another embodiment of a cap 119' with a threaded shaft is shown in FIG. 9, and in this embodiment the bearing surface 139' is concave.

Figure 10:
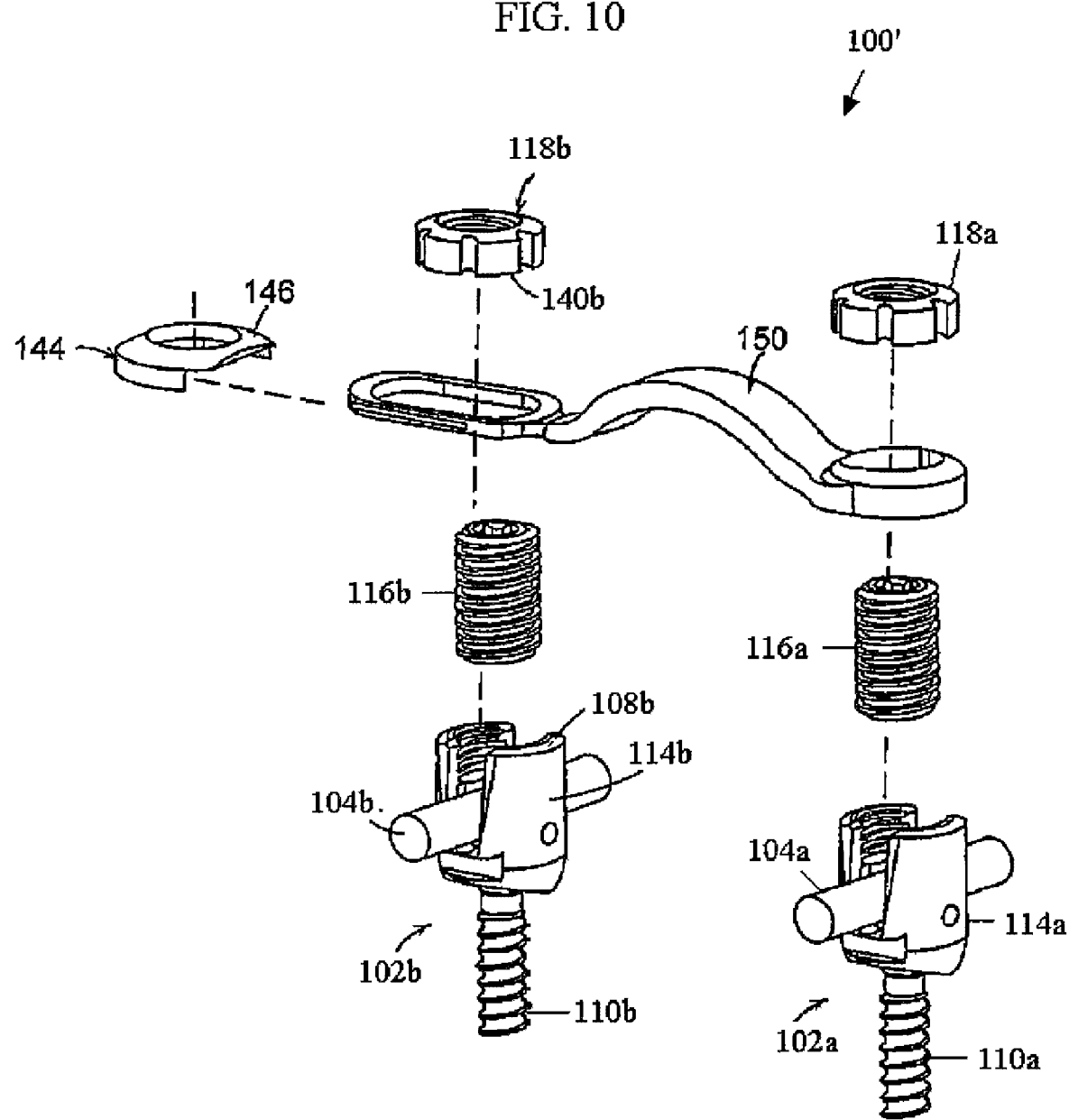
FIG. 10 is an exploded perspective view of another embodiment of a spinal fixation system that includes a floating washer.

FIG. 10 illustrates another embodiment of a spinal fixation system 100'. In this embodiment, spinal fixation 100' includes a floating washer 144 to allow the connecting plate 150 to be used with bone anchors 110a, 110b positioned at various distances from one another. As shown in more detail in FIGS. 11A-11C, the floating washer 144 includes a bearing surface 146 that mates with a distal bearing surface 140 of cap 118, and rails 148 that slidably engage the connecting plate 150. In use, the floating washer 144 can be slide onto the connecting plate 150, which as shown in FIG. 10 has an elongate slot formed thereon. The floating washer 144 can be positioned as desired relative to the elongated slot, and then mated to the bone anchor 102b using cap 118b and set screw 116b. The connecting plate 150 is thereby fixed to the bone anchor 102b by compression between the floating washer 144 and the bone anchor 102b.

Figure 13A:
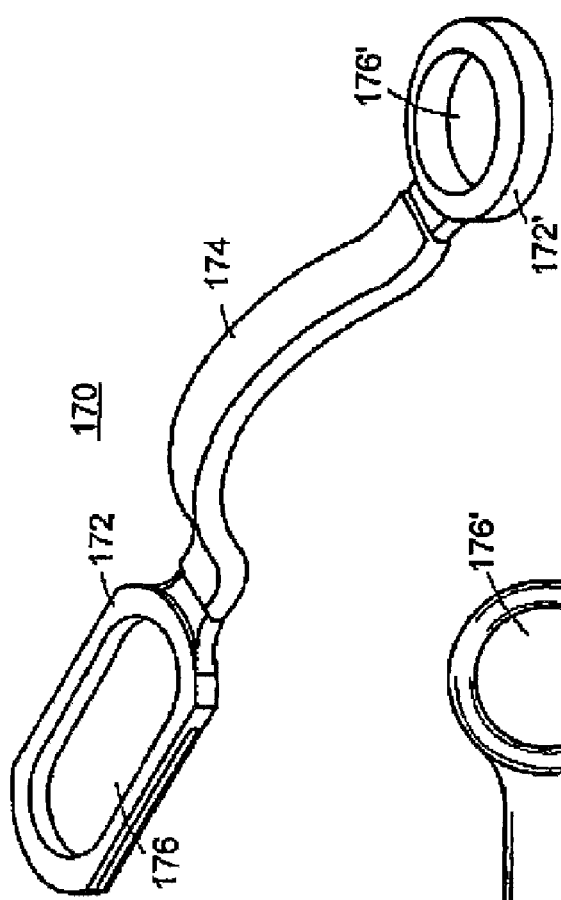
FIG. 13A is a perspective view of another embodiment of a connecting plate.
Figure 13B:
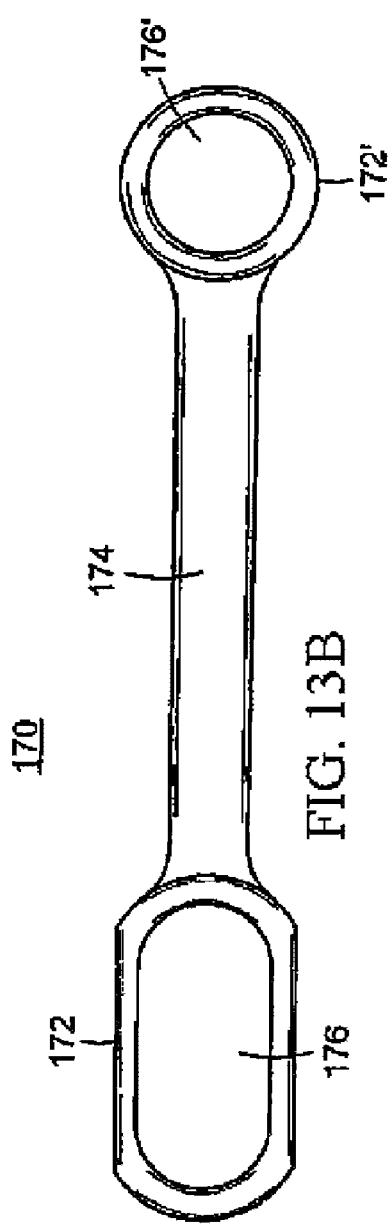
FIG. 13B is a top view of the connecting plate shown in FIG. 13A.
Figure 13C:
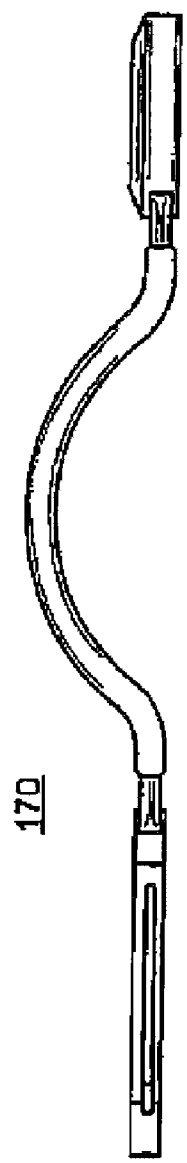
FIG. 13C is a side view of the connecting plate shown in FIG. 13A.
Figure 14A:
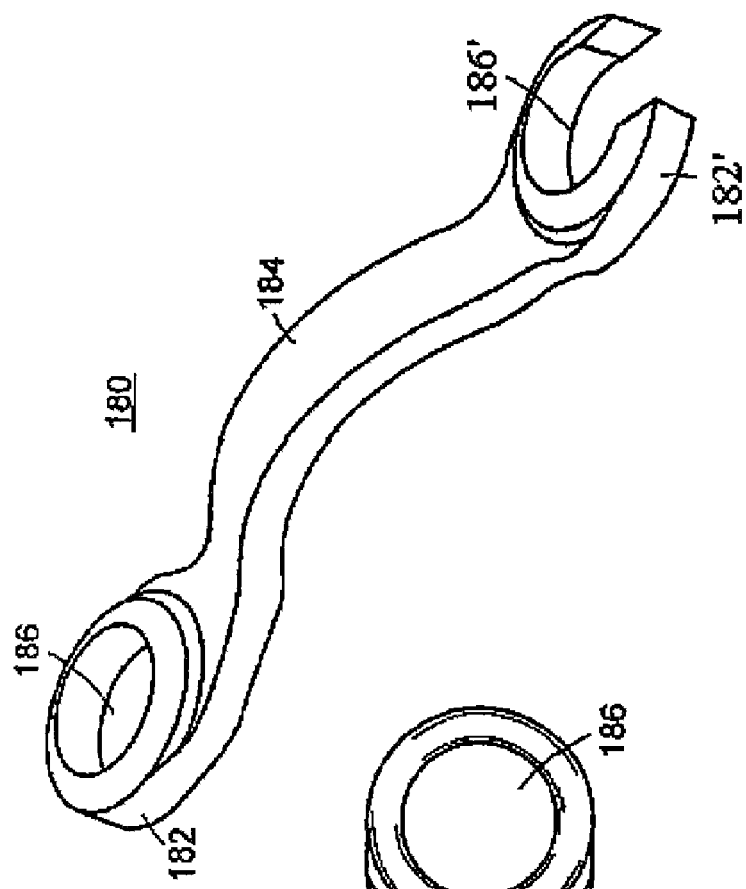
FIG. 14A is a perspective view of yet another embodiment of a connecting plate.
Figure 14B:
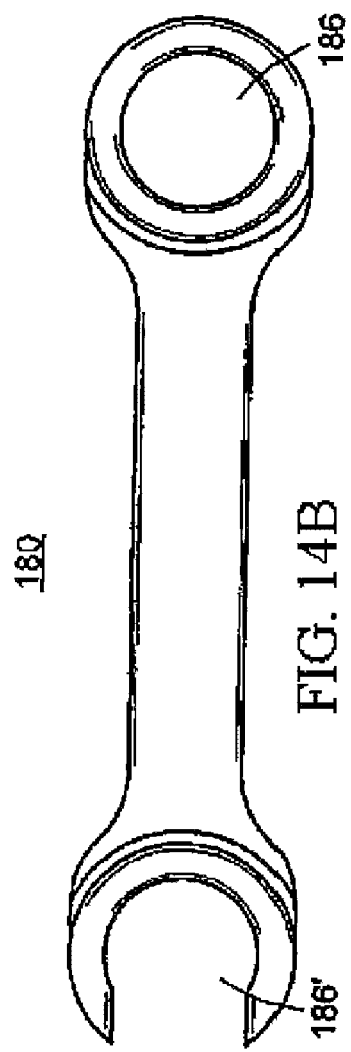
FIG. 14B is a top view of the connecting plate shown in FIG. 14A.
Figure 14C:
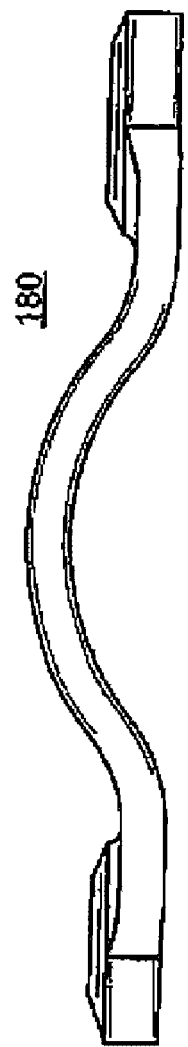
FIG. 14C is a side view of the connecting plate shown in FIG. 14A.

As previously indicated, the connecting plate can have a variety of other configurations. For example, as indicated above, the connecting plate 150 shown in FIG. 10 has one end with an elongate slot formed therein for allowing the bone anchor 102b to be mated to the connecting plate 150 at a selected position. FIGS. 12A-14C illustrate various other exemplary embodiments of a connecting plate. In the embodiment shown in FIGS. 12A-12C, the connecting plate 160 includes a spanning portion 164 extending between opposed ends, each end having an elongated opening 166, 166' formed therein. The ends can also includes rails 162 configured to mate with a washer 144. FIGS. 13A-13C illustrate another embodiment of a connecting plate 170. In this embodiment, the spanning portion 174 extends between a first end 172 having an elongate slot 176 formed therein and having side rails configured to mate with a washer 144, and a second end 172' having a circular opening 176' formed therein. In yet another embodiment, as shown in FIGS. 14A-

14C, the connecting plate 180 can include a spanning portion 184 extending between a first end 182 with a circular opening 186, and a second end 182' with an open-ended opening 186'.

In other embodiments, the connecting member can be in the form of a rod rather than a plate. A band clamp or other fastening element can be used to mate the rod to the bone anchors. FIGS. 15A-B illustrate a spinal fixation system 500 having first and second bone anchors 502a, 502b, first and second band clamps 504a, 504b, a connecting rod 506, and first and second dovetail threaded post subassemblies 508a, 508b. The threaded post subassemblies 508a, 508b mate to the bone anchors 502a, 502b, respectively, and the band clamps 504a, 504b mate the connecting rod 506 to the subassemblies 508a, 508b, respectively. Other features and methods of operation of system 500 are substantially similar to those disclosed herein for system 100.

During operation, referring back to the embodiment shown in FIGS. 1A and 1B, for example, the first and second bone anchors 102a, 102b can be implanted in opposed lateral sides of a vertebra. One or more additional bone anchors can be implanted in one or more adjacent vertebra. A spinal fixation element, such as spinal rods 104a, 104b can be positioned within the rod-receiving portion 114a, 114b of each bone anchor 102a, 102b, and optionally within the rod-receiving portion of one or more bone anchors implanted in one or more adjacent vertebrae. The sets screws 116a, 116b are then mated to the bone anchors 102a, 102b to lock the rod therein. The connecting plate 106 can then be positioned to span between the bone anchors 102a, 102b. In particular, the first end 122a of the connecting plate 106 can be positioned over the first set screw 116a, and the second end 122b of the connecting plate 106 can be positioned over the second set screw 116b. Caps 118a, 118b can then be threaded onto the set screws 116a, 116b to lock the connecting plate 106 to the bone anchors 102a, 102b, thereby stabilizing the bone anchors 102a, 102b.

Figure 16A:
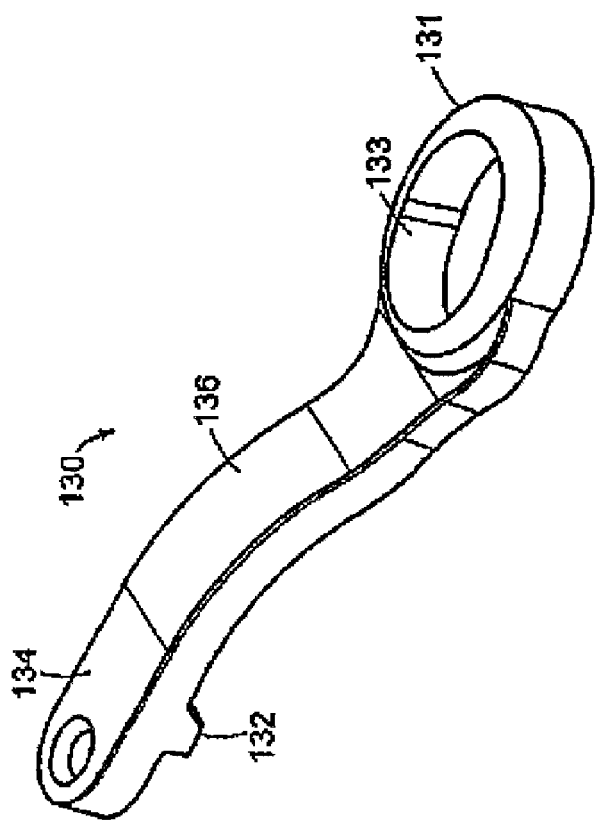
FIG. 16A is a perspective view of another embodiment of a connecting plate.
Figure 16B:
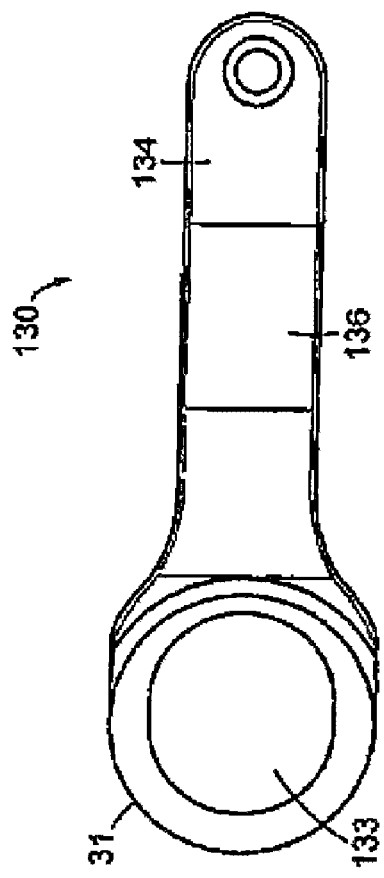
FIG. 16B is a top view of the connecting plate shown in FIG. 16A.
Figure 16C:
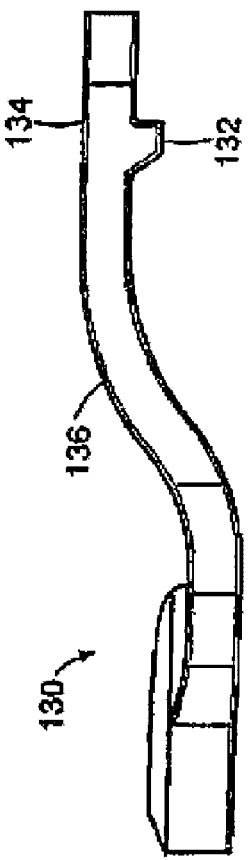
FIG. 16C is a side view of the connecting plate shown in FIG. 16A.
Figure 17A:
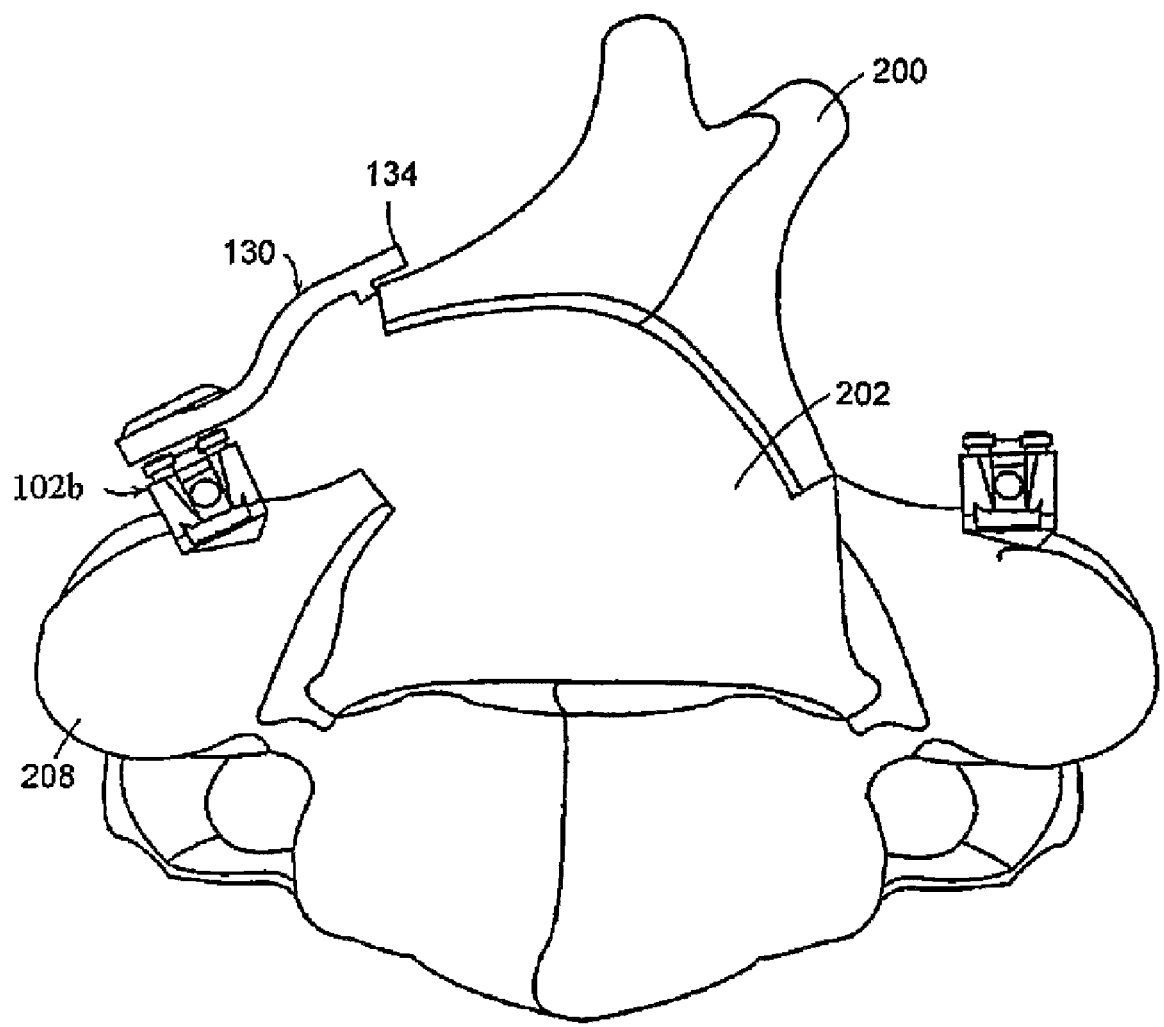
FIG. 17A is an illustration of the connecting plate shown in FIG. 16A mated to a vertebra in a patient's spine for supporting the spinous process in the rotated position during a partial laminoplasty.

In another embodiment the connecting plate can be adapted to span between a bone anchor and a posterior element of a vertebra. For example, FIGS. 16A-16C illustrate a connecting plate 130 having a spanning portion 136 with a buttress 132 formed on an inferior surface 134. In use, as shown in FIG. 17A, the connecting plate 160 can be used to decompress the spinal canal. As shown, a first dissection 204 is made in a posterior element 200 of a vertebra, and the posterior element 200 is then moved to expand the spinal canal 202. The connecting plate 130 is then coupled to a bone anchor 102b implanted in the vertebra and to the posterior element 200 to maintain the posterior element 200 in a fixed position. In one embodiment, the posterior element 200 can be a portion of the lamina of the vertebra. In another embodiment, the posterior element 200 can be the spinous process of the vertebra.

Figure 17B:
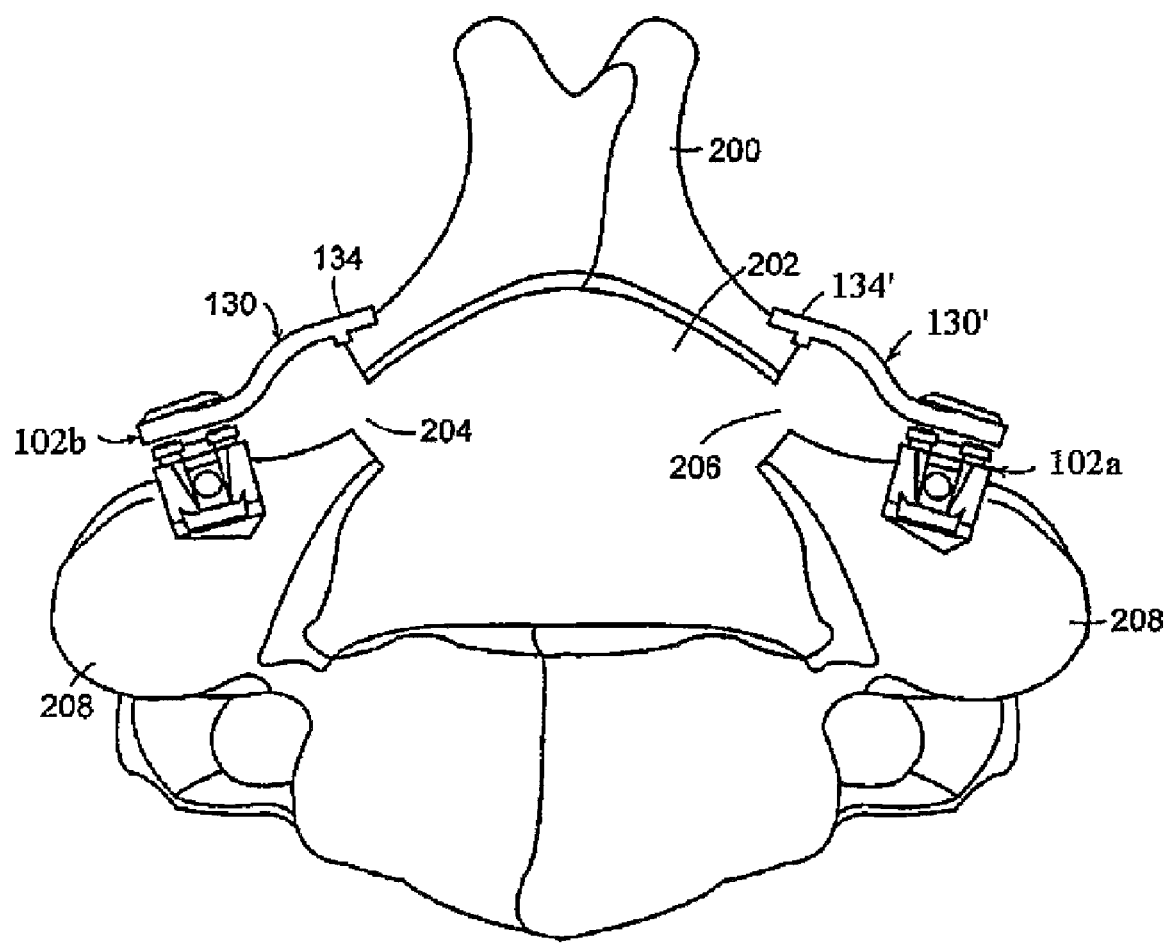
FIG. 17B is an illustration of the connecting plate shown in FIG. 16 and a second connecting plate mated to opposed lateral sides of a vertebra in a patient's spine for supporting the spinous process during a total laminoplasty.

The method can also include making a second dissection 206 on the contralateral side of the posterior element 200 opposite to the first cut 204, as shown in FIG. 17B. The posterior element 200 is then moved to expand the second cut 206, and a second connecting plate 130' is then coupled to a second bone anchor 102' and the posterior element 200' to maintain the second cut 206 in the expanded position. As a result, the spinal canal is enlarged. In an exemplary embodiment, the bone anchors 102a, 102b are implanted in the lateral mass 208 of the vertebra, for example in the pedicles.

While the previous embodiments relate to cross connectors for mating two bone anchors, or for mating a bone anchor to a posterior element, in another embodiment a cross-connector is provided for mating a bone anchor to a spinal fixation element, such as a rod, cable, tether, etc. Some injuries allow only a single bone anchor to be implanted on a lateral side of a vertebra, preventing a second bone anchoring from being implanted on an opposed lateral side of the vertebra. However, it may be desirable to provide additional support to the bone anchor that is implanted in the vertebra. Accordingly, a head-to-rod cross connector is provided for coupling a bone anchor implanted on a first lateral side of a vertebra to a spinal fixation element, such as a spinal rod, spanning across an opposed lateral side of the vertebra.

Figure 18A:
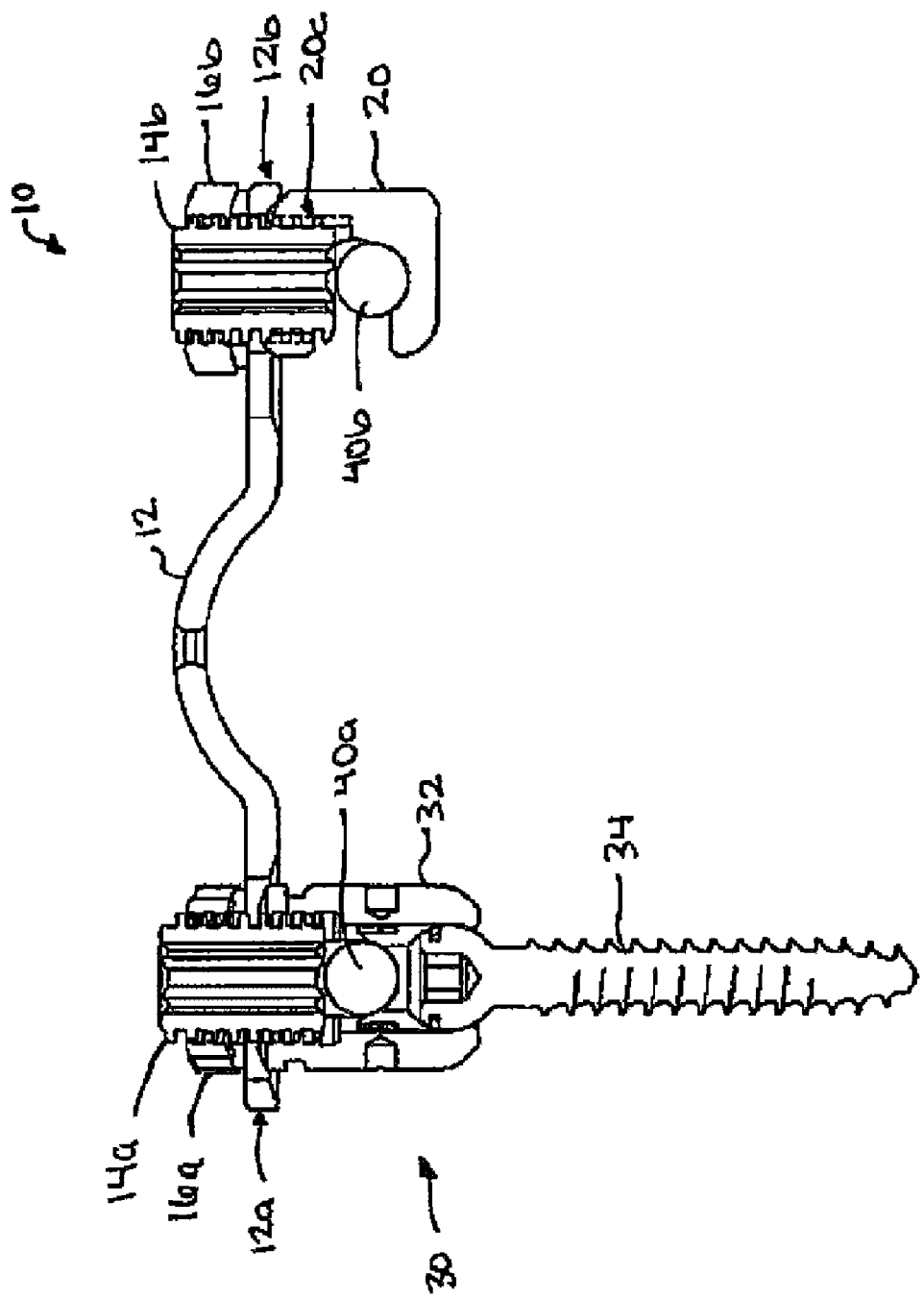
FIG. 18A is a cross-sectional view of another embodiment of a spinal stabilization system having a connecting plate with a first end mated to a bone anchor and a second end with a side-loading coupling member mated directly to a spinal fixation element.
Figure 18B:
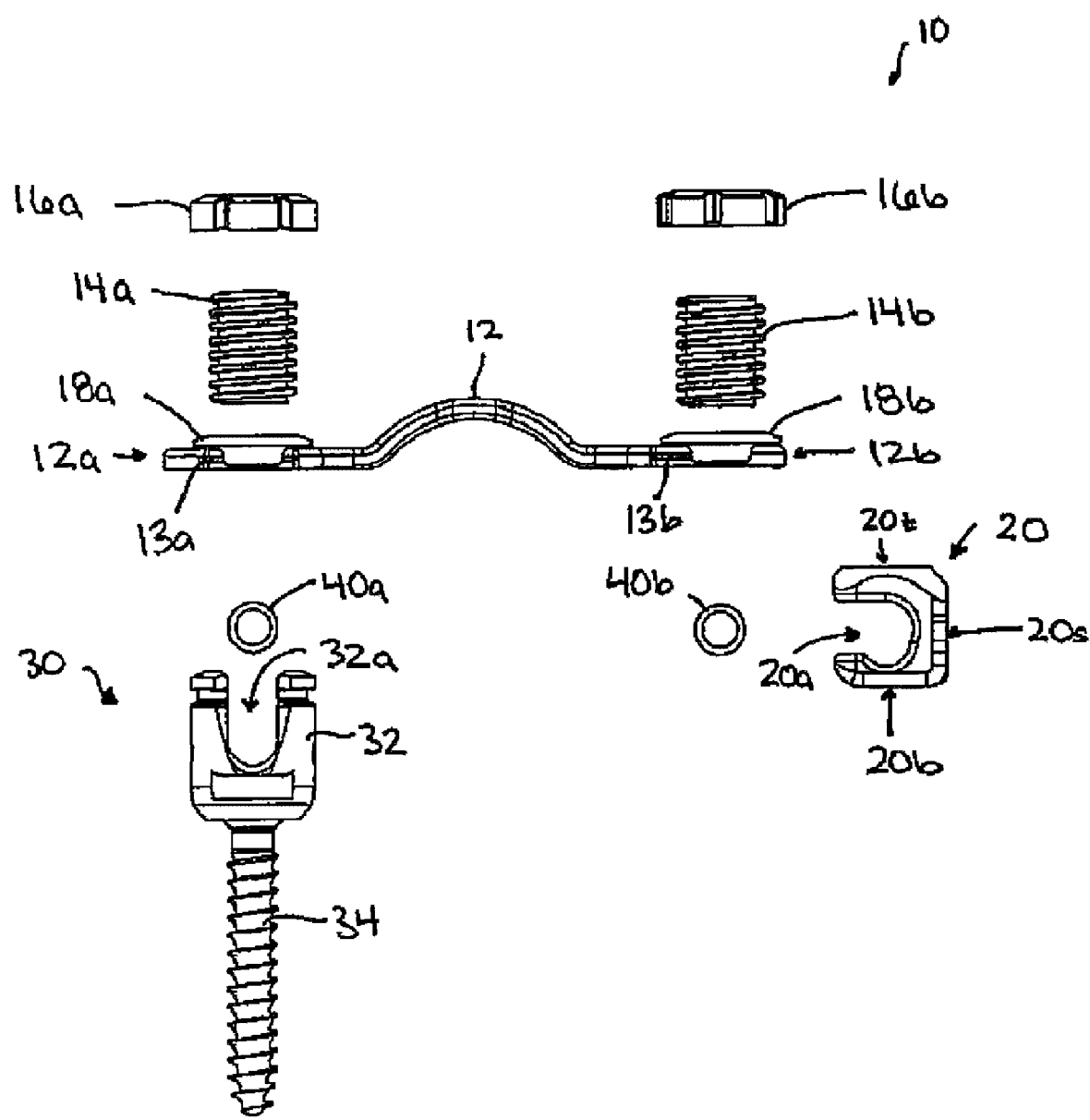
FIG. 18B is an exploded view of the spinal stabilization system shown in FIG. 18A.
Figure 18C:
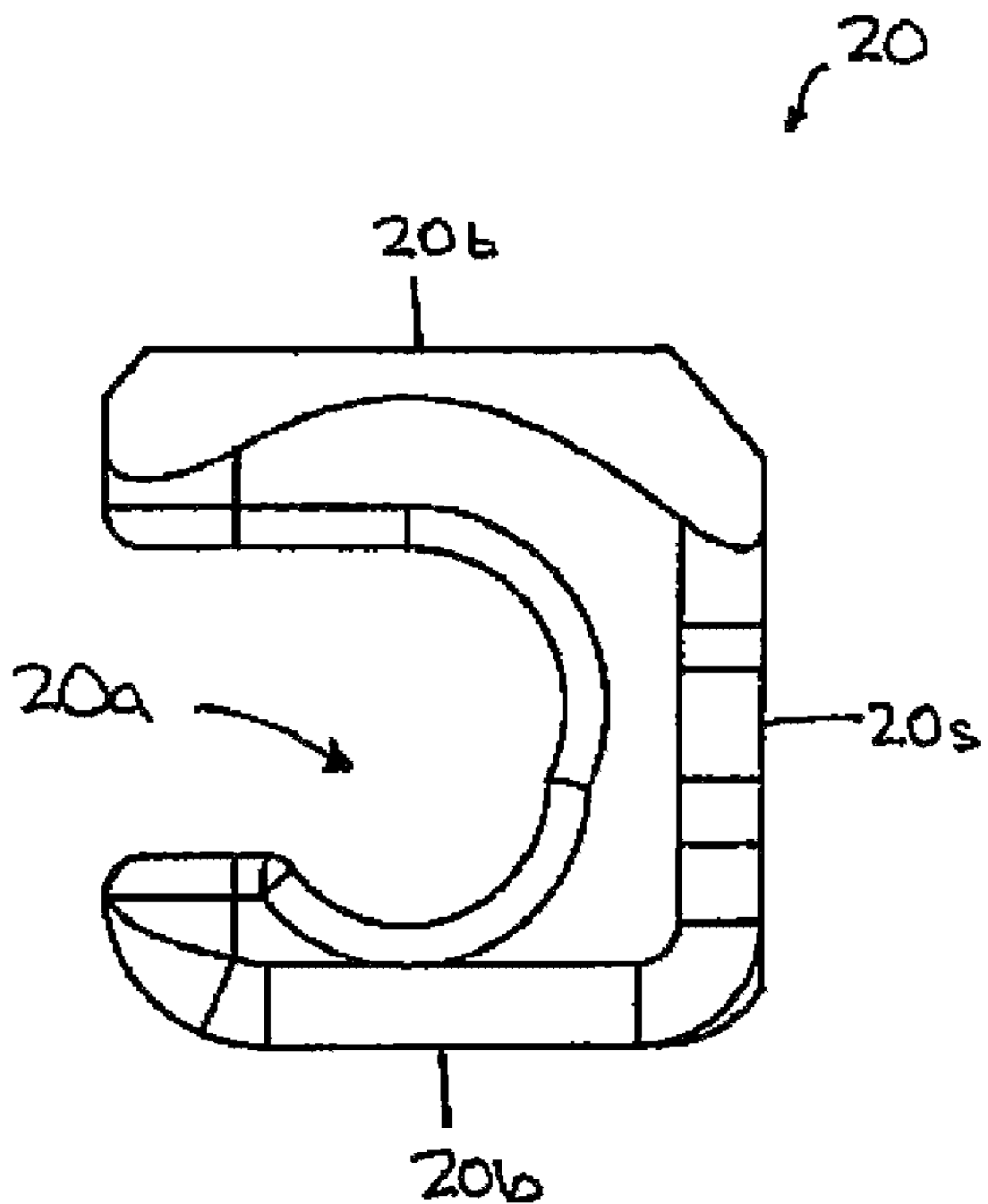
FIG. 18C is a side view of the side-loading coupling member of the spinal stabilization system shown in FIG. 18A.

FIGS. 18A-18C illustrate one exemplary embodiment of a spinal stabilization system 10 having a head-to-rod cross connector 12. The spinal stabilization system 10 is similar to the previously described systems, except that one end of the cross connector can mate directly to a spinal fixation element, such as a spinal rod, without anchoring to bone. In particular, the second end 12b of the cross connector 12 includes a coupling member 20 for mating the second end 12b of the cross connector 12 directly to a spinal fixation element, such as spinal rod 40b as shown. The first end 12a of the cross connector 12, as well as the bone screw 30, spinal rod 40a, and fastening element, which includes set screw 14a and locking cap 16a, are similar to previously described embodiments, and thus they will not be discussed in detail with respect to FIGS. 18A-18B. The cross connector 12 can also include floating washers 18a, 18b, as shown, to facilitate mating of the cross connector 12 to the first and second spinal rods 40a, 40b at a particular location. Exemplary floating washers were previously described with respect to FIGS. 10-11C.

The coupling member 20 can have a variety of configurations, and it can be adapted to mate to a spinal rod 40a and to the second end 12b of the cross connector 12 using a variety of techniques. In the illustrated embodiment, as shown in FIG. 18A-18C, the coupling member 20 is in the form of a housing having a rod-receiving recess 20a formed therein for seating a spinal fixation element, such as spinal rod 40b. The illustrated rod-receiving recess 20a has a substantially concave shape to seat a cylindrical rod 40b extending therethrough, and it is defined by a top wall 20t, a bottom wall 20b, and a sidewall 20s connecting the top and bottom walls 20t, 20b. As a result, the coupling member 20 is a side-loading coupling member 20, i.e., it loads onto a spinal rod 40b from the side.

The coupling member 20 can mate to the second end 12 of the cross connector 12 using a variety of mating techniques. In the illustrated exemplary embodiment, the coupling member 20 includes an opening 20c formed in the top wall 20t thereof for receiving a fastening element, such as set screw 12b. The opening 20c can extend into the rod-receiving recess 20a to allow the set screw 12b to abut against a spinal rod 40b disposed therein, thereby locking the rod 40b to the coupling member 20, and thus to the cross connector 12. The fastening element can also including a locking cap 16b, similar to those previously described, that mates to the set screw 14b and that bears against the cross connector 12 to lock the cross connector 12 to the coupling member 20. A person skilled in the art will appreciate that the fastening element can have a variety of other configurations, including those described herein as well as those known in the art. The cross connector 12 can also have a variety of other configurations, and it can include other features to facilitate mating to the coupling member 20.

In use, as shown in FIG. 18A, the first end 12a of the coupling member 20 can be mated to a bone anchor 30 that is implanted in a lateral side of a first vertebra. In particular, a set screw 14a can be inserted through a thru-bore or opening 13a formed in the first end 12a of the cross connector 12, and it can be threaded into the rod-receiving portion 32 of the bone screw 30 to lock a spinal rod 40a in the rod-receiving recess 32a. A locking cap 16a can be threaded onto an opposed end of the set screw 14a to lock the cross connector 12 to the bone anchor 30. The second end 12b of the cross connector 12 can be mated to a spinal rod 40b that extends substantially parallel to spinal rod 40a on an opposed lateral side of the first vertebra, and that is not anchored to the first vertebra. In particular, the coupling member 20 can be side loaded onto the spinal rod 40b, and a set screw 14b can be inserted through an opening or thru-bore 13b formed in the first end of the cross connector 12 and into the opening 20c formed in the coupling member 20 to lock the rod 40b within the rod receiving recess 20a of the coupling member 20. The cross connector 12 can alternatively be placed over the set screw 14b after the set screw 14b is mated to the coupling member 20. The locking cap 16b can be threaded onto an opposed end of the set screw 14b to lock the cross connector 12 to the coupling member 20. The coupling member thus provides additional support to a spinal stabilization system implanted in a patient's spine without requiring both ends of the cross connector to anchor to bone. A person skilled in the art will appreciate that both end of the cross connector can mate to first and second spinal fixation elements, such as spinal rods, without anchoring to bone. For example, first and second coupling member can be used to mate a cross connector to first and second spinal rods extending along opposed lateral sides of a vertebra.

Figure 19A:
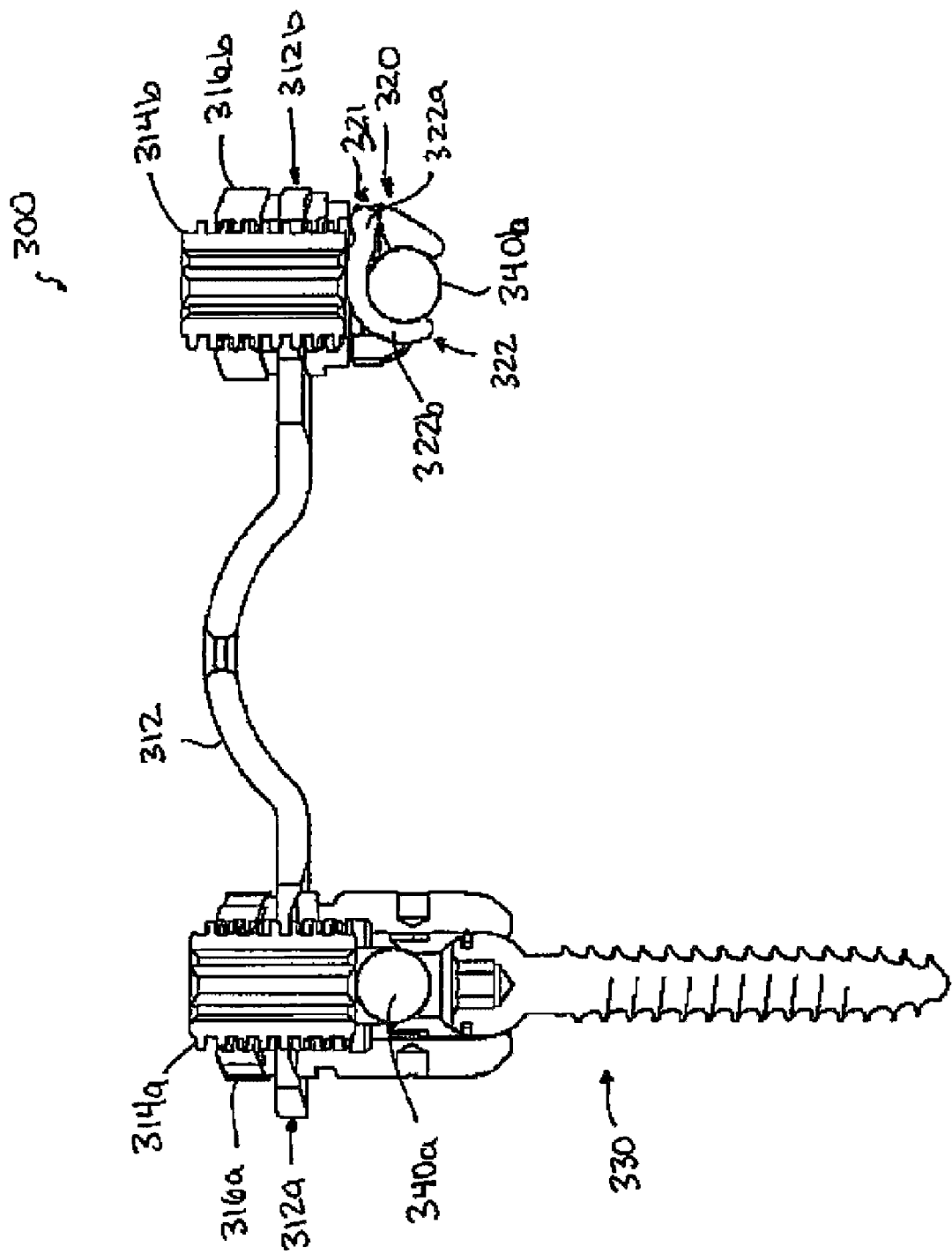
FIG. 19A is a cross-sectional view of another embodiment of a spinal stabilization system having a connecting plate with a first end mated to a bone anchor and a second end with a top-loading coupling member mated directly to a spinal fixation element.
Figure 19B:
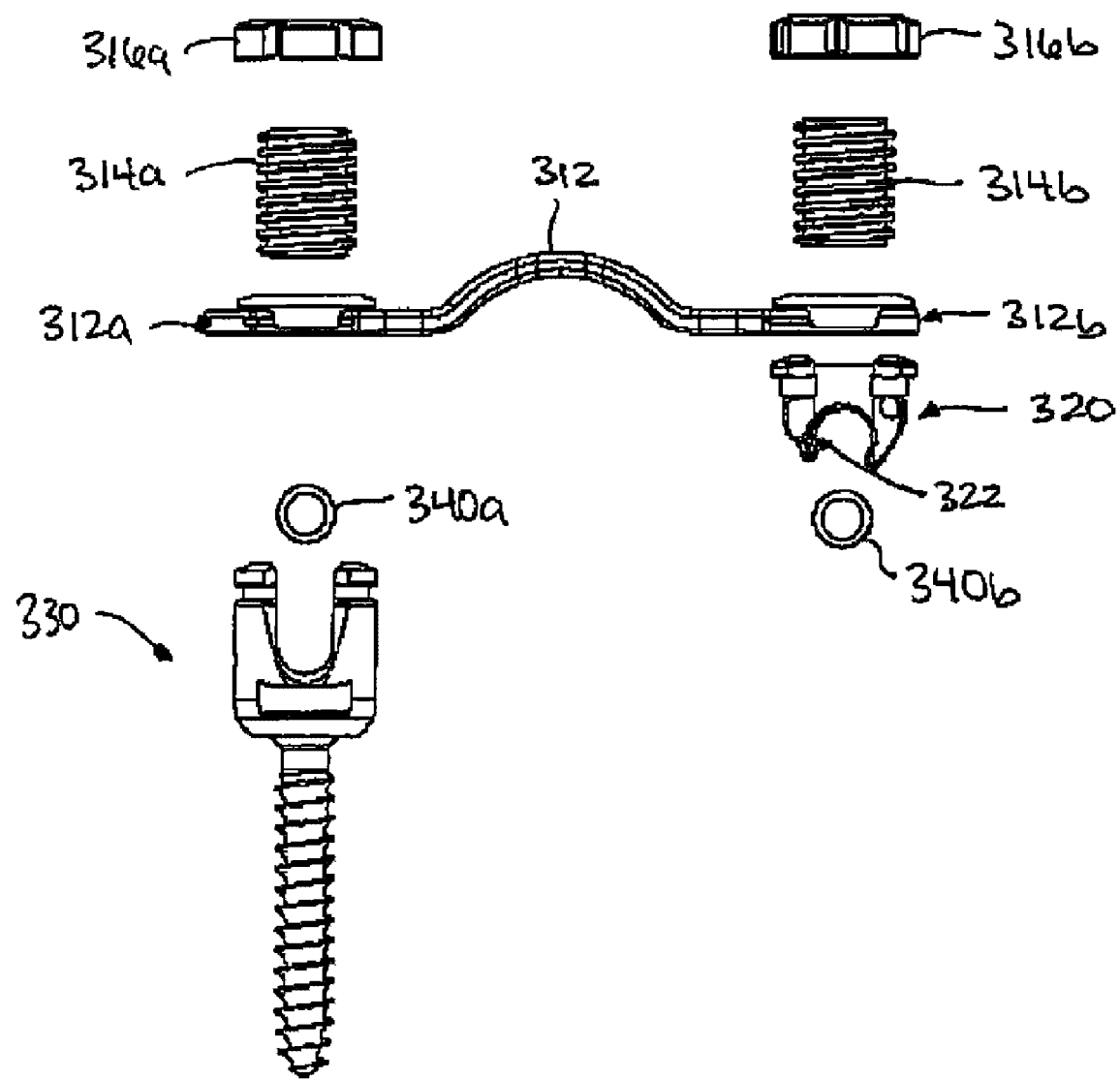
FIG. 19B is an exploded view of the spinal stabilization system shown in FIG. 19A.
Figure 19C:
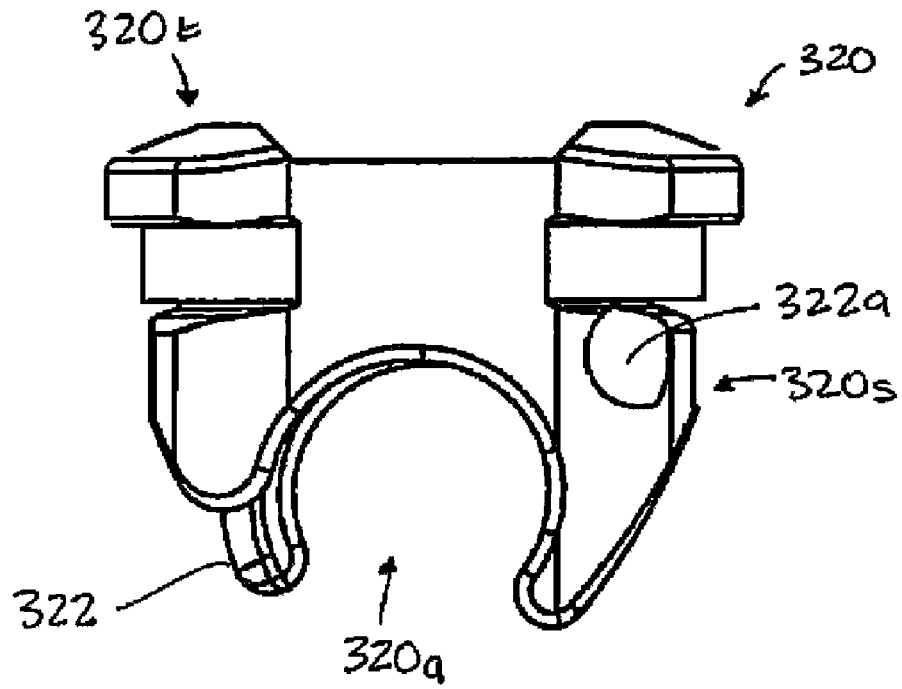
FIG. 19C is a side view of the top-loading coupling member of the spinal stabilization system shown in FIG. 19A.

As indicated above, the coupling member can have a variety of other configurations, and various techniques can be used to mate the coupling member to a spinal fixation element, such as a spinal rod, and to the cross connector. FIGS. 19A-19C illustrate another embodiment of coupling member 320. The coupling member 320 is illustrated as part of a spinal stabilization system 300 which, like previous embodiments, generally includes a cross connector 312 having a first end 312a that is adapted to mate to a bone anchor 330, and a second end 312b that is adapted to mate to a coupling member 320. A first fastening element, which includes a set screw 314a and a locking cap 316a, is provided for locking the first end 312a of the cross connector 312 to the bone screw 330, and for locking a spinal rod 140a in the rod-receiving portion of the bone screw 330, and a second fastening element, which includes a set screw 314b and a locking cap 316b, is provided for locking the second end 312b of the cross connector 312 to the coupling member 320. In the embodiment shown in FIGS. 18a-18C, the set screw 14a was effective to directly contact the spinal rod 40a to lock the spinal rod 40a in the rod-receiving recess 20a of the coupling member 20. In this embodiment, the set screw 314a does not directly engage the spinal rod 340a, but rather the coupling member 320 includes a locking arm 322 disposed therein for engaging the spinal rod 340a. The coupling member 320 is also top loading, rather than side loading.

The locking arm 322, which is best shown in FIG. 19A, can have a variety of shapes and sizes, but in an exemplary embodiment it is adapted to extend around at least a portion of a spinal rod 340a disposed within the rod-receiving recess 320a, and it is adapted to engage the rod 340a when the set screw 314b is mated to the coupling member 320a. In particular, the locking arm 322 can have an elongate configuration with a first end 322a that is adapted to be pivotally disposed within an elongate opening 321 formed in a sidewall 320s of the coupling member 320, and a second or terminal end 322b that is curved and that extends into the rod-receiving recess 320a of the coupling member 320a. The locking arm 322 can also extend across the path of the opening formed in the top wall 320t of the coupling member 320 that receives the set screw 314b. As a result, when the set screw 314b is inserted through the opening in the top wall 320t of the coupling member 320 it will bear down on the locking arm 322, thereby causing the curved terminal end of the locking arm 322 to pivot downward and engage the spinal rod 340b.

In use, the coupling member 320a is inserted over the spinal rod 340b, i.e., the spinal rod 340b is bottom loaded into the rod-receiving recess 320a of the coupling member 320. The set screw 314b is then inserted through the opening formed in the second end 312b of the cross connector 312 and into the opening formed in the coupling member 320a to bear against the locking arm 322, thereby causing the locking arm 322 to engage and lock the spinal rod 340a within the rod-receiving recess 320a of the coupling member 320. The cross connector 312 can alternatively be placed over the set screw 314b after the set screw 314b is mated to the coupling member 320. The locking cap 316b can then be threaded onto the set screw 314b to lock the cross connector 312 to the coupling member 320.

Figure 20:
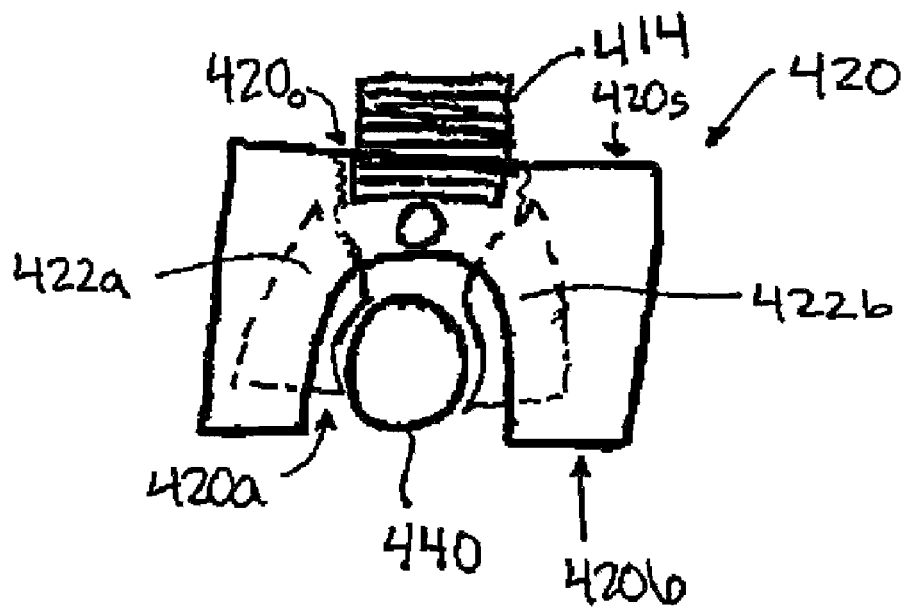
FIG. 20 is a side view of another embodiment of a top-loading coupling member having wedges disposed therein and adapted to engage a spinal fixation element.

FIG. 20 illustrates yet another embodiment of a coupling member 420. In this embodiment, the coupling member 420 includes two rod-engaging members or wedges 422a, 422b slidably disposed within the coupling member 420. The wedges 422a, 422b can have a variety of configurations and they can be mated to or disposed within the coupling member 420 using a variety of techniques, but they are preferably effective to move linearly in response to a force applied thereto by a set screw 414 to lock a spinal fixation rod 420 within the rod-receiving recess 420a of the coupling member 420. In an exemplary embodiment, the coupling member 42 includes first and second receiving cavities (not shown) formed therein for slidably seating the wedges 422a, 422b. The first and second cavities preferably extend between the opening 420o formed in the top wall 420s of the coupling member 420 that receives the set screw 414, and the rod-receiving recess 420a. The cavities are also preferably spaced a distance apart from a bottom surface 420b of the coupling member 420 to allow the wedges 422a, 422b to be retained within the coupling member 420.

In use, the coupling member 420 can be top loaded onto a spinal rod 420a, and the set screw 414 can be inserted, e.g., threaded, into the opening 420o in the coupling member 420. The set screw 414 will thus bear against the opposed wedges 422a, 422b, thereby driving the wedges 422a, 422b linearly such that the extend into the rod-receiving recess 420a. As a result, the wedges 422a, 422b will engage the spinal rod 440, thereby locking the rod 420a to the coupling member 420. As previously described, a cross connector can be mated to the coupling member 420 using a locking cap of other locking mechanism.

Figure 21A:
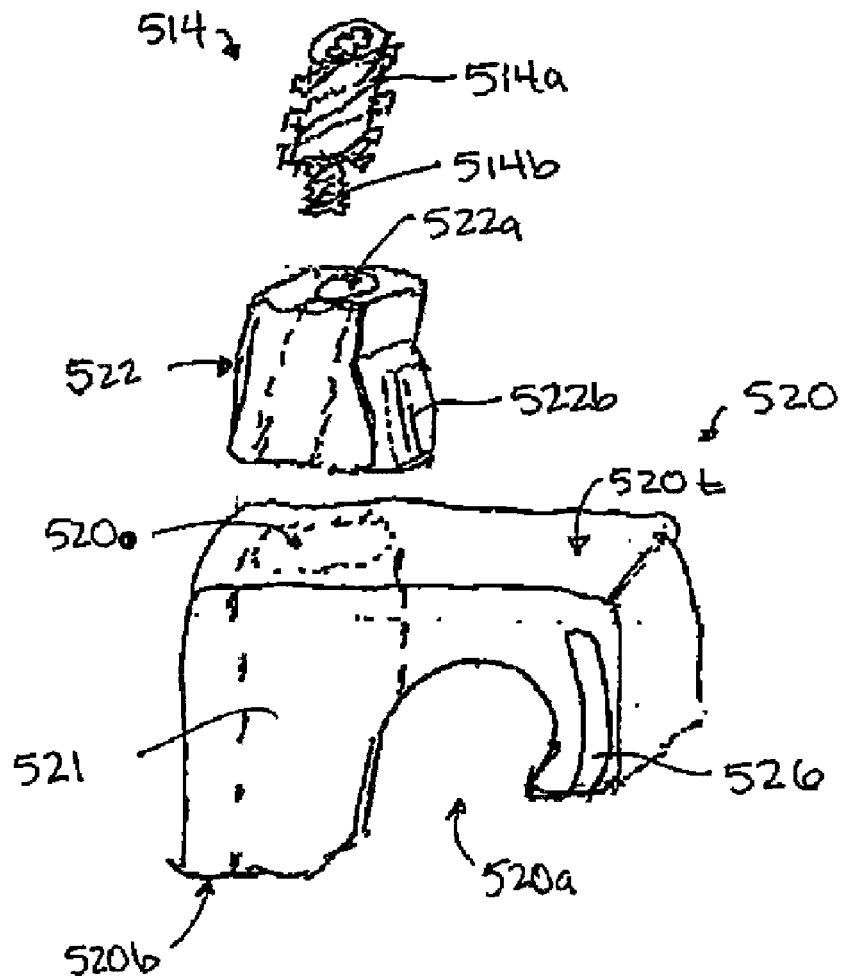
FIG. 21A is an exploded view of another embodiment of a top-loading coupling member having an offset wedge that is adapted to engage a spinal fixation element.
Figure 21B:
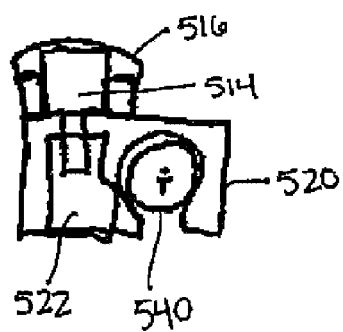
FIG. 21B is a cross-sectional, assembled view of the top-loading coupling member shown in FIG. 21A.

FIGS. 21A-21B illustrate yet another embodiment of a coupling member 520 that can be used to couple a cross connector to a spinal rod without anchoring the cross connector to bone. In this embodiment, the coupling member 520 includes a single wedge or shoe 522 disposed therein. The shoe 522 is disposed within a cavity 521 that is laterally offset from the rod receiving recess 520a formed in the coupling member 520. In particular, the cavity 512 extends from a top wall 520t toward a bottom wall 520b. The cavity 512 can terminate prior to the bottom wall 520b such that the bottom wall 520 is effective to retain the shoe 522 therein. The shoe 522 is adapted to sit within the cavity 521 and is movable from a distal position to a proximal position, i.e., the shoe 522 moves from a resting position adjacent to the bottom wall 520b toward the top wall 520a. Movement of the shoe 522 can be achieved using a set screw 514 that is inserted through an opening 520o formed in the top surface 520t of the coupling member 520, and through an opening 522a formed in the shoe 522. As the set screw 514 is threaded or otherwise mated to the shoe 522, the set screw 514 can pull the shoe 522 toward the top wall 520t. In an exemplary embodiment, the set screw 514 can include a proximal portion 514a that is adapted to mate with and engage the coupling member 520, and a distal portion 514b that is adapted to mate with and engage the shoe 522. The proximal and distal portions 514a, 514b can have a different size, e.g., diameter, thread pitch, etc. Such a configuration allows the set screw 514 to move the shoe 522 proximally while maintaining the coupling member 520 in a substantially fixed position. As a result of the movement of the shoe 522, a wedge-shaped protrusion 522b extending into the rod-receiving recess 502a of the coupling member 520 will move toward the top wall 520t, thereby engaging a spinal rod 540 disposed within the rod-receiving recess 520a, as shown in FIG. 21B. A locking cap 516 can then be applied to the proximal portion 514a of the set screw 514 to mate a cross connector to the coupling member 520.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal fixation system, comprising:
   a cross connector configured to span between opposed lateral sides of a vertebra and having first and second ends;
   a coupling member mated to the first end of the cross connector and having a rod-receiving recess formed therein for coupling to a spinal rod without anchoring to bone; and
   a bone anchor having:
      a shaft for engaging bone; and
      a head having opposed arms with a rod-receiving recess formed therebetween for receiving a spinal rod;
   wherein the second end of the cross connector has a distal surface that bears against a proximal terminal end surface of each of the opposed arms of the head of the bone anchor.

2. The system of claim 1, wherein rod-receiving recess formed in the coupling member is defined by a top wall, a bottom wall, and a side wall connecting the top and bottom walls.

3. The system of claim 2, wherein the top wall includes a thru-bore formed therein for receiving a fastening element adapted to mate the coupling member to the cross connector.

4. The system of claim 3, further comprising a fastening element adapted to extend through an opening formed in the first end of the cross connector and to extend into the thru-bore formed in the top wall of the coupling member for mating the coupling member to the cross connector.

5. The system of claim 4, wherein the fastening element extends into the rod-receiving recess to lock a spinal rod disposed therein to the coupling member.

6. The system of claim 1, wherein rod-receiving recess formed in the coupling member is defined by a top wall and first and second side walls extending from opposed sides of the top wall.

7. The system of claim 6, wherein the top wall includes a thru-bore formed therein for receiving a fastening element adapted to mate the coupling member to the cross connector.

8. The system of claim 7, further comprising a locking arm extending into the rod-receiving recess and adapted to extend around at least a portion of a rod disposed within the rod-receiving recess.

9. The system of claim 8, wherein the locking arm extends through one of the first and second side walls of the coupling member.

10. The system of claim 8, further comprising a fastening element adapted to extend through an opening formed in the first end of the cross connector and to extend into the thru-bore formed in the top wall of the coupling member to abut against the locking arm and thereby lock a rod within the rod-receiving recess of the cross connector.

11. The system of claim 1, further comprising a fastening element adapted to extend through an opening formed in the first end of the cross connector and into an opening formed in the coupling member to mate the coupling member to the cross connector.

12. The system of claim 11, wherein the fastening element comprises a set screw and a cap that mates to the set screw.

13. The system of claim 11, wherein the fastening element is further configured to lock a rod within the rod-receiving recess of the coupling member.

14. The system of claim 13, wherein the coupling member includes at least one movable member adapted to move in response to a force applied thereto by the fastening element to engage a rod disposed within the rod-receiving recess.

15. The system of claim 13, wherein the opening formed in the coupling member for receiving the fastening element is offset from a central axis of the coupling member.

16. The system of claim 13, wherein the coupling member includes a wedge disposed therein and adapted to be engaged by the fastening element such that the wedge moves to engage a rod disposed within the rod receiving recess of the coupling member.

17. A spinal fixation system, comprising:
   a cross connector configured to span between opposed lateral sides of a vertebra and having first and second ends;
   a substantially C-shaped coupling member having opposed top and bottom walls and a side wall connecting the top and bottom walls, the top, bottom, and side walls defining a rod-receiving recess, and the top wall including a thru-bore formed therein;
   a fastening element adapted to mate the first end of the cross connector to the coupling member, and adapted to extend through the thru-bore formed in the top wall and into the rod-receiving recess of the coupling member to lock a spinal rod therein; and
   a bone anchor having a shaft for engaging bone and a head with opposed arms, the second end of the cross connector having a distal surface that bears against a proximal terminal end surface on each of the opposed arms of the head of the bone anchor.

18. A method for spinal stabilization, comprising:
   coupling a first end of a cross connector to a head of a bone anchor to anchor the first end of the cross connector to a first vertebra, the bone anchor having a first spinal rod extending therethrough and the cross connector having a distal surface that bears against a proximal terminal end surface on each of first and second opposed arms on a head of the bone anchor; and
   coupling a second end of the cross connector to a second spinal rod without anchoring the second end of the cross connector to the first vertebra.

19. The method of claim 18, wherein coupling a second end of the cross connector to a second spinal rod comprises positioning the second spinal rod within a rod receiving recess of a coupling member, and inserting a fastening element through the second end of the cross connector and into an opening formed in the coupling member to lock the spinal rod, coupling member, and cross connector to one another.

20. The method of claim 19, wherein the spinal rod is side-loaded into a rod-receiving recess formed in a sidewall of the coupling member, and wherein the fastening element is inserted into an opening formed in a top wall of the coupling member.

21. The method of claim 19, wherein the spinal rod is bottom-loaded into a rod-receiving recess formed in a bottom wall of the coupling member, and wherein the fastening element is inserted into an opening formed in a top wall of the coupling member.

* * * * *